United States Patent
Oraevsky et al.

(10) Patent No.: US 7,500,953 B2
(45) Date of Patent: Mar. 10, 2009

(54) HIGH CONTRAST OPTOACOUSTIC IMAGING USING NANOPARTICLES

(75) Inventors: Alexander A. Oraevsky, Houston, TX (US); Paul M. Henrichs, Houston, TX (US)

(73) Assignee: Seno Medical Instruments, Inc., San Antonio, TX (US)

( * ) Notice: Subject to any disclaimer, the term of this patent is extended or adjusted under 35 U.S.C. 154(b) by 848 days.

(21) Appl. No.: 10/764,213

(22) Filed: Jan. 23, 2004

(65) Prior Publication Data

US 2005/0175540 A1  Aug. 11, 2005

Related U.S. Application Data

(60) Provisional application No. 60/442,369, filed on Jan. 25, 2003.

(51) Int. Cl.
*A61B 8/14* (2006.01)

(52) U.S. Cl. .............................. 600/458; 73/585; 367/87

(58) Field of Classification Search ......... 600/407–480, 600/310; 367/87
See application file for complete search history.

(56) References Cited

U.S. PATENT DOCUMENTS

| | | | |
|---|---|---|---|
| 5,447,710 A | 9/1995 | Na et al. | |
| 5,472,683 A | 12/1995 | Illig | |
| 5,500,204 A | 3/1996 | Osifo | |

(Continued)

FOREIGN PATENT DOCUMENTS

EP  0601618  6/1994

(Continued)

OTHER PUBLICATIONS

Link et al., "Shape and size dependence of radiative, non-radiative and photothermal properties of gold nanocrystals", 2000, International Reviews in Physical Chemistry, vol. 19, No. 3, pp. 409-453, ISSN 0144-235X.*

A. A. Oraevsky, Laser based optoacoustic imaging in biological tissues, Proc. SPIE 1994; 2134A: 122-128.

(Continued)

*Primary Examiner*—Brian L. Casler
*Assistant Examiner*—Nasir Shahrestani
(74) *Attorney, Agent, or Firm*—Benjamin Aaron Adler

(57) ABSTRACT

A method of enhancing detection for a specific object in a body. A nanoparticulate is administered to the body for location in an area to be explored for detection of the object, if present. The nanoparticulate is at least partially metallic, has a formed non-spherical shape having a minimal characteristic dimension in the range from about 1 to about 3000 nanometers, and has a formed composition capable of producing thermal pressure either in the nanoparticulate or in the object greater than the object could produce in the absence of the nanoparticulate. Electromagnetic radiation is directed into the body. The electromagnetic radiation has a specific wavelength or spectrum of wavelengths in the range from 300 nm to 300 mm selected so that the wavelength or wavelength spectrum is longer by a factor of at least 3 than the minimum characteristic dimension of the nanoparticulate. The nanoparticulate absorbs the electromagnetic radiation more than would one or more non-aggregated spherically shaped particles of the same total volume with a composition identical to the nanoparticulate. The nanoparticulate produces an enhanced optoacoustic signal resulting from the absorption that is received and converted into an electronic signal and presented for assessment of the at least one parameter by a human or a machine.

4 Claims, 10 Drawing Sheets

U.S. PATENT DOCUMENTS

| | | | |
|---|---|---|---|
| 5,521,218 | A | 5/1996 | Osifo |
| 5,525,328 | A | 6/1996 | Bacon et al. |
| 5,543,133 | A | 8/1996 | Swanson et al. |
| 5,560,932 | A | 10/1996 | Bagchi et al. |
| 5,573,783 | A | 11/1996 | Desleno et al. |
| 5,580,579 | A | 12/1996 | Ruddy et al. |
| 5,840,023 | A | 11/1998 | Oraevsky et al. |
| 6,090,858 | A | 7/2000 | El-Sayed |
| 6,123,923 | A | 9/2000 | Unger et al. |
| 6,139,819 | A | 10/2000 | Unger et al. |
| 6,143,276 | A | 11/2000 | Unger et al. |
| 6,180,085 | B1 | 1/2001 | Achilefu et al. |
| 6,180,087 | B1 | 1/2001 | Achilefu et al. |
| 6,183,726 | B1 | 2/2001 | Achilefu et al. |
| 6,190,641 | B1 | 2/2001 | Achilefu |
| 6,264,914 | B1 | 7/2001 | Klaveness et al. |
| 6,264,917 | B1 | 7/2001 | Klaveness et al. |
| 6,264,919 | B1 | 7/2001 | Achilefu et al. |
| 6,264,920 | B1 | 7/2001 | Achilefu et al. |
| 6,270,806 | B1 | 8/2001 | Liversidge et al. |
| 6,331,289 | B1 | 12/2001 | Klaveness et al. |
| 6,344,272 | B1 * | 2/2002 | Oldenburg et al. ......... 428/403 |
| 6,375,931 | B2 | 4/2002 | Bronstein et al. |
| 6,395,257 | B1 | 5/2002 | Achilefu et al. |
| 6,403,056 | B1 | 6/2002 | Unger |
| 6,428,811 | B1 | 8/2002 | West et al. |
| 6,662,040 | B1 * | 12/2003 | Henrichs et al. ............ 600/431 |
| 7,129,091 | B2 * | 10/2006 | Ismagilov et al. ............ 436/34 |
| 2001/0002275 | A1 | 5/2001 | Oldenburg et al. |
| 2002/0022004 | A1 | 2/2002 | Licha et al. |
| 2002/0034537 | A1 | 3/2002 | Schulze et al. |
| 2002/0044909 | A1 | 4/2002 | Achilefu et al. |
| 2002/0103517 | A1 | 8/2002 | West et al. |
| 2002/0132045 | A1 | 9/2002 | Halas et al. |
| 2002/0159951 | A1 * | 10/2002 | Unger et al. ............... 424/9.51 |
| 2002/0160195 | A1 | 10/2002 | Halas et al. |
| 2005/0019266 | A1 * | 1/2005 | Unger et al. ............. 424/9.321 |

FOREIGN PATENT DOCUMENTS

| | | |
|---|---|---|
| EP | 0602700 | 6/1994 |
| EP | 0808175 | 11/1997 |
| WO | WO9857667 | 12/1998 |
| WO | WO0106257 | 1/2001 |
| WO | WO02059226 | 8/2002 |

OTHER PUBLICATIONS

A. A. Oraevsky, Lateral and z-axial resolution in laser optoacoustic imaging with ultrasonic transducers, Proc. SPIE, 1995, 2389, 198-208, (Appendix).

A. A. Oraevsky, et al. "Breast Cancer Diagnostics by Laser Opto-Acoustic Tomography", OSA Trends ***in Optical Imaging and Photon Migration, 1996, v.2, pp. 316-321.

A. A. Oraevsky, et al. Measurement of tissue optical properties by time-resolved detection of laser-induced transient stress, Applied Optics, 1997, 36(1): 402-415.

S. Link, et al. Spectral properties & relaxation dynamics, surface plasmon electronic oscillations in gold and silver nanodots and nanorods, J. Phys. Chem. B, 1999, 103, 8410.

S. Link, et al, Shape and size dependence of radiative, non-radiative and photothermal properties of gold nanocrystals, Int. Rev. Phy. Chem., 19 (3), 409-453 (2000).

A. A. Oraevsky, et al. Optoacoustic supercontrast for early cancer detection, Proc. SPIE 2001; 4256, 179-187.

A. A. Oraevsky, et al. Enhancement of optoacoustic tissue contrast with absorbing nanoparticles, European Conference on Biomedical Optics, Proc. SPIE 2001, 4434, 60-69.

M.A. El-Sayed, Some interesting properties of metals confined in time and nanometer space of different shapes, Accounts of Chemical Research, 34 (1), 257-264 (2001).

A. A. Oraevsky, et al. Opto-acoustic imaging of blood for the visualization and diagnosis of breast cancer, Proc. SPIE 2002; 4618: 81-93.

A. A. Oraevsky, et al. On a plasmon resonance in ellipsoidal nanoparticles, Quantum Electronics, 32 (1) 79-82 (2002).

* cited by examiner $p_\perp = a_2 / a_1 = b_2 / b_1$    $p_\parallel = c_2 / c_1$ $q_{1,2} = a_{1,2} / c_{1,2} = 1/\zeta_{1,2}$    $e_{1,2} = (1-q_{1,2}^2)^{1/2} = 1/\xi_{1,2}$

HIGH CONTRAST OPTOACOUSTIC IMAGING USING NANOPARTICLES

REFERENCE TO RELATED APPLICATION

This application claims the benefit of 35 U.S.C. 111 (b) Provisional Patent Application Ser. No. 60/442,369, filed Jan. 25, 2003, and entitled, "Contrast Agents for Optoacoustic Imaging."

STATEMENT REGARDING FEDERALLY SPONSERED RESEARCH OR DEVELOPEMENT

The government may own rights to this invention pursuant to Grant No. R33 CA095883 from the National Cancer Institute (NCI), Dept. of Health and Human Services.

BACKGROUND OF THE INVENTION

The present invention relates to optoacoustic imaging employing nanoparticles to enhance detection of objects in a body. The invention has applications that include imaging for medical reasons.

Optoacoustic imaging is to be distinguished from optical imaging. In optical imaging a body is irradiated with light in the visible or infrared wavelength ranges. Transmitted or reflected light in the same ranges is detected to generate images. Optical imaging suffers from the severe disadvantage that resolution of the image is inherently low, because light, whether in the visible or near infrared spectrum, is strongly scattered in the body through interaction with local inhomogeneities.

Optoacoustic methods of imaging rely not on detection of visible or infrared light irradiated onto a body, but on the sensitive detection of ultrasonic waves induced inside the body by optical radiation. Optoacoustic imaging fundamentally is based on the optical properties of the tissue it detects, but it relies on the sensitive detection of induced ultrasonic waves rather than light itself for image generation. Its resolution is like that of an ultrasound image rather than that of an optical image. Optoacoustic imaging (Oraevsky et al., U.S. Pat. No. 5,840,023) is the use of lasers to generate light of a narrow spectrum or specific wavelengths to irradiate the tissue to be examined, a so-called laser optoacoustic imaging system ("LOIS"). The principle of the LOIS system is that the preferential absorption of short laser pulses of irradiation by tissues containing an absorbing chromophore, such as hemoglobin in blood-rich cancerous tumors, generates pressure disturbances centered on the absorption sites. The rapid increase of the local pressure at the absorption sites leads to pressure pulse propagating through the bulk of the tissue according to the rules of sound transmission. The shapes of the pressure waves retain information about the shapes of the regions of origin (Oraevsky, 1993; Diebold, 1994).

The term "optoacoustic imaging" as used herein applies to any imaging method in which electromagnetic radiation generates a detectable pressure wave or sound from which an image is calculated. Optoacoustic imaging is equivalent in meaning to the term, "photoacoustic imaging," used by others to refer to the same technology. However, the term "optoacoustic" is not universally so used, and indeed has been combined with the word "imaging" by Unger and Wu in U.S. Pat. No. 6,123,923 to describe a different imaging technology (light irradiation of their method plays no role in the generation of a detected acoustic signal). As used herein, the term "optoacoustic imaging" as used by Unger and Wu in U.S. Pat. No. 6,123,923 has no relevance to light irradiated optoacoustic imaging.

To those uninitiated in this art, it may be surprising that it is possible to generate sound from light with high efficiency. In fact, optoacoustic imaging is quite sensitive as an imaging method. The temperature increase produced by the absorption of the light energy that is necessary to produce the detected signal is only a small fraction of a temperature degree. Nevertheless, the pressure generated by this local temperature increase generates a readily detectable acoustic wave. Recent advances in optoacoustic imaging have allowed the visualization, quantitative characterization and real-time monitoring in the depth of human tissue with sensitivity and resolution superior to that of pure optical methods (Oraevsky et al. in U.S. Pat. Nos. 5,840,023, 6,405,069, and 6,498,942). Some of these advances have come through the use of contrast agents for optoacoustic imaging, as was anticipated by Oraevsky et al. in U.S. Pat. No. 5,840,023 and was taught specifically for both soluble and insoluble contrast agents by Henrichs et al. in U.S. Pat. No. 6,662,040 and PCT publication WO9857667. Subsequently, other inventors have taught the use of specific classes of soluble contrast agents for optoacoustic imaging (U.S. Pat. Nos. 6,180,085; 6,180,087; 6,183,726; 6,190,641; 6,264,920; 6,264,919; and 6,395,257; and in U.S. Patent Application 20020044909, now U.S. Pat. No. 6,641,798).

Unlike optical imaging, the diffusion of light by the tissues produced by strong light scattering is not a problem for optoacoustic imaging. Indeed, light diffusion actually helps to bathe the interior of the tissues uniformly with the radiation. Furthermore, the extent to which an internal tissue component, such as a cancerous tumor, absorbs light is enhanced by the presence of scattering centers within that component. These centers lengthen the effective path length followed by a photon in passing through the tissue component. Thus, the chance that the photon will be absorbed by tissue molecular constituents is increased. It is the ultrasound produced by the absorption of the light that provides the information necessary for image calculation. Thus, the resolution of optoacoustic imaging is closer to that for ultrasound imaging than it is to that for optical imaging. Nevertheless, optoacoustic imaging retains the high contrast of pure optical imaging. It has the best features of both optical and ultrasound imaging.

Recent advances have greatly enhanced the ability of optical imaging, especially with near-infrared radiation, to show features in the human breast and other organs. There have been a number of patents describing novel contrast agents and novel uses of contrast agents with respect to optical imaging. Licha et al. teach the use of colloidal dye suspensions for optical imaging (U.S. Pat. App. 2002022004). Some of the inventors of contrast agents for optical imaging have recognized that particulate contrast agents will have utility. For example, Klaveness et al. teach the use of particulate contrast agents, which may or may not comprise a light-absorbing component, in optical imaging (Eur. Pat. EP0808175). Particulate materials are well known as contrast agents for X-ray (and ultrasound) imaging. (Encapsulated gas bubbles form the most significant class of contrast agents for ultrasonic imaging.) There is a long series of patents relating to the stabilization of nanoparticles in X-ray contrast agents (U.S. Pat. Nos. 5,472,683, 5,500,204, 5,521,218, 5,525,328, 5,543,133, 5,447,710, 5,560,932, 5,573,783, 5,580,579, 6,270,806 and Eur. Pat. Nos. EP0601618 and EP0602700). West et al. describe the preparation of nanoshells comprising a particle core covered with a metal shell have optical properties that can make them useful as contrast agents for optical imaging (U.S. Pat. Nos. 6,344,272, 6,438,811, U.S. Pat. App. Publication No. 20020160195, now U.S. Pat. No. 6,660,381, U.S. Pat. App. Publication Nos. 20010002275 and 20020132045, and PCT WO0106257 and PCT WO02059226). They also describe the use of nanoshells of arbitrary shape as contrast agents in optical imaging (U.S. Pat. App. Publication No. 2002013517, now U.S. Pat. No. 6,530,944).

There would be real benefit in having a light based detection system that can detect objects as small as 1 mm. Imaging resolution on the order of 1 mm is necessary for tumor detection at a stage when it is readily treatable. The general wisdom is that smaller size tumors will be easier to cure. There is a significant medical need for imaging methods that boost both sensitivity and resolution to about 1 mm or smaller. Greater sensitivity will allow the detection of both smaller tumors and tumors that have reduced blood content because they are in an early stage of development or because of therapeutic interventions. Tumors in the prostate or breast or in other organs at such an early stage of development may be termed "nascent tumors." Nascent tumors differ from precancerous lesions in they contain identifiable cancerous cells. However, they have not yet developed into recognizable tumor masses. In particular, they have not yet developed the extensive vascular network that is characteristic of many larger solid tumors. For detection of nascent cancerous tumors, it may no longer be sufficient to rely on differences in the blood content and normal tissue. The blood content of a nascent cancerous tumor is likely to be similar to that of normal tissue. An alternative detection strategy will be required. Currently, however, neither pure optical imaging can nor prior optoacoustic imaging could detect tumors as small as 1 mm. It is unlikely that images of the interior of the human breast or any other thick part of the body will ever be produced by pure optical imaging with a resolution of about 1 mm.

Other than detection of cancers, near infrared optoacoustic imaging has important other advantages, as will be further detailed below in describing various embodiments of our invention.

SUMMARY OF THE INVENTION

Oraevsky et al. [Proc. SPIE 2001; 4256: 179-187; Proc. SPIE2001; 4434: 60-69.] predicted that various nanoparticles can enhance tissue contrast in optoacoustic imaging, however, specific types of nanoparticles most beneficial for optoacoustic imaging were not disclosed.

We have now discovered a way in which to optoacoustically detect the presence of objects as small as 1 mm and smaller in a body which can be penetrated by electromagnetic radiation. We have discovered that at least partially metallic nanoparticulates fabricated or manipulated to be non-spherical not only will shift the optical absorption spectrum into the near infrared range for deeper penetration into a body but also will both narrow the absorption band and simultaneously increase the effective absorbance, in certain instances by about an order of magnitude or more, thereby greatly increasing the optoacoustic efficacy of the nanoparticulate, making the manipulated nanoparticulate a very high contrast optoacoustic imaging agent. In accordance with our discoveries, effective acoustical response to electromagnetic radiation is increased by tailoring the choice of the composition, non-spherical shape and size of nanoparticulates to maximize both the optical absorbance of the particles at the irradiation wavelength(s) and the optoacoustic pressure produced in response to absorbed electromagnetic energy.

This invention comprises a method of enhancing detection for a specific object in a body. A nanoparticulate is administered to the body for detection of the object, if present. The nanoparticulate is at least partially metallic, has a formed non-spherical shape having a minimal characteristic dimension in the range from about 1 to about 3000 nanometers, and has a formed composition capable of producing thermal pressure either in the nanoparticulate or in the object greater than the object could produce in the absence of the nanoparticulate.

In accordance with the invention, electromagnetic radiation is directed onto the body. The electromagnetic radiation has a specific wavelength or spectrum of wavelengths in the range from 3 nm to 300 mm selected so that the wavelength or wavelength spectrum is longer by a factor of at least 3 than the minimum characteristic dimension of the nanoparticulate. The nanoparticulate absorbs the electromagnetic radiation more than would one or more non-aggregated spherically shaped particles of the same total volume with a composition identical to the nanoparticulate. The nanoparticulate by such absorption produces an enhanced optoacoustic signal resulting from the absorption. The optoacoustic signal can then be received and converted into an electronic signal characterized by at least one parameter selected from amplitude, frequency, phase, temporal profile, time of arrival, frequency spectrum, or a combination of any one or more of such parameters. The electronic signal may then be presented for assessment of the at least one parameter by a human or a machine.

By the term "nanoparticulate" as used herein, is generic for a single nanoparticle, a collection of nanoparticles, or a nanoparticle aggregate. Thus in describing a nanoparticulate as at least partially metallic, as having a formed non-spherical shape having a minimal characteristic dimension in the range from about 1 to about 3000 nanometers, and as having a formed composition capable of producing thermal pressure either in the nanoparticulate or in the object greater than the object could produce in the absence of the nanoparticulate, it is conveyed that (i) a single nanoparticle may have such properties, or (ii) that a collection of nanoparticles may have nanoparticles most probably having such properties, or (iii) that an aggregate of nanoparticles has such properties.

Shape

The non-spherical shape of the nanoparticulate is one that causes the nanoparticulate to absorb electromagnetic radiation of certain criteria more than spherically shaped nanoparticles of the same total volume and even the same composition as the non-spherical nanoparticulate. Non-spherical nanoparticualtes will have an elongate shape, i.e., they have any geometrical shape in which one dimension is longer than the other two dimensions in three-dimensional space. By the phrase "minimum characteristic dimension" is meant the one dimension which is longer than the other two dimensions in three-dimensional space.

The term "formed shape" for characterizing the at least partially metallic non-spherical nanoparticulate used in this invention means that the shape is one fabricated or manipulated to increase one dimension more than the others in three dimensional space. For example, the nanoparticulate may be rod shaped or substantially ellipsoidal in at least one dimension. An elongate nanoparticulate used in this invention suitably has an aspect ratio of from about 2 to about 10. By the phase "aspect ratio" in the context of the shape of a nanoparticulate in this invention is meant the longest dimension of the nanoparticulate divided by the shortest dimension of the nanoparticulate. For example, in the case of a rod shape, the aspect ratio is the length over the width. Advantageously, the longest dimension of the elongate nanoparticulate is in the range from about 2 nanometers to about 200 nanometers.

The formed shape may be fractal or non-fractal. Fractal structures may be regular or irregular. Thus the structure may be any of various extremely irregular curves or shapes for which any suitably chosen part is similar in shape to a given larger or smaller part when magnified or reduced to the same size. Suitable fractal structures are two-dimensional stars with an even number of points. (A two-dimensional star is a three dimensional star in which the "z" axis has a length small enough to be ignored, that is, the star is "flat". In this case, the minimum characteristic dimension is the length between opposite points of the star even if those points intersect a circle circumscribed about the star.) Preferred are three-dimensional stars with even number of points. An even number of points yields a greater absorption due to the fact that two points produce a structure similar to an ellipsoid (dipole).

In more Euclidian shapes, shapes for the nanoparticulates include cylinders (rods), cones, polyhedra, ellipsoids and other shapes that are non-spherical.

The shape is engineered for longer length in one dimension in order to provide sufficient shift of an electromagnetic absorption maximum towards longer wavelengths compared with spherical (or otherwise fully symmetrical) nanoparticles, to yield desirable absorption at a selected wavelength or selected spread of wavelengths which are capable of penetrating the body.

Preferred shapes of the nanoparticles used in the practice of the invention are cylindrical rods and prolate ellipsoids. Thus, the invention encompasses the use of contrast agents for optoacoustic imaging, comprising rod-shaped metal particles, aggregates of rod-shaped metal particles, prolate ellipsoids, or aggregates of prolate ellipsoids.

For metal rods, the aspect ratio, that is the ratio of the length of a rod to its diameter, is the critical parameter controlling the match to the wavelength of irradiation. For prolate ellipsoids, the aspect ratio is the ratio of the longest cross-sectional diameter to the smallest cross-sectional diameter. As is the case for the particle weights, there will generally be a range of aspect ratios for the metal rods.

As mentioned, the partially metallic nanoparticulate may be a collection of nanoparticles. In an embodiment a collection of nanoparticles has a most probable aspect ratio of from about 2 to about 10. The "most-probable" aspect ratio is the aspect ratio most likely to be found when an individual particle is selected from the mixture.

For irradiation at 757 nm, the most-probable aspect ratio of gold cylindrical particles used in the practice of the invention preferably will be between 3.0 and 4.5. More preferably, the most-probable aspect ratio will be 3.4 and 4.1. Thus, the invention encompasses the use of contrast agents for optoacoustic imaging at 757 nm comprising rod-shaped gold particles with most-probable aspect ratios preferably between 3.4 and 4.1.

For irradiation at 1100 nm, the most-probable aspect ratio of gold cylindrical particles used in the practice of the invention preferably will be between 6.0 and 10.0. More preferably, the most-probable aspect ratio will be 7.0 and 9.0. Thus, the invention encompasses the use of contrast agents for optoacoustic imaging at 757 nm comprising rod-shaped gold particles with most-probable aspect ratios preferably between 7.0 and 9.0.

In analogy to the definitions for the number-average and weight-average particle weights, it is possible to define number-average and weight-average aspect ratios $NR=\Sigma(n_i R_i)/\Sigma(n_j)$ and $WR=\Sigma(n_i R_i^2)/\Sigma(n_j R_j)$, respectively, where $R_i$ is the aspect ratio for an individual particle selected from the particle mixture. The ratio of the weight-average to the number-average aspect ratios is a useful measure of the width of the aspect ratio distribution. The invention encompasses any use of contrast agents for optoacoustic imaging comprising metal rods or aggregates of metal rods for which the ratio of the weight average of particle aspect ratios to the number average of particle aspect ratios is preferably less than 10, more preferably less than 5, and most preferably less than 1.5.

A collection of nanoparticle used in this invention may be combinations of nanoparticles of one shape with nanoparticles of another shape to form nanoparticulate geometries capable of absorbing a selected specific wavelength or range of wavelengths. Where the elongate nanoparticles are in a collection of nanoparticles, the collection suitably has a most probable aspect ratio of from about 2 to about 10.

The invention anticipates the use of contrast agents sensitive to two different irradiation wavelengths. In this case, the contrast agent will comprise particles with two different mean aspect ratios.

A non-spherical nanoparticulate comprising a nanoparticle aggregate does not require that the nanoparticles of the aggregate be non-spherical. The nanoparticles of the aggregate may comprise spherical nanoparticles ordered in a structure to have the properties of the nanoparticulate of this invention. In an embodiment, a nanoparticulate aggregate is so ordered and the nanoparticles are at least partially coated with organic material, such organic material suitably comprising genetic material to ordain such order.

Dimension

In the practice of the invention, the shape of individual nanoparticulates or a collection of nanoparticles is more crucial than the dimension or size of the nanoparticulates. However, for medical or biological applications, the dimension of the nanoparticulates is crucial in controlling the biological properties of the nanoparticulates, especially the clearance rate from blood and tissues. Thus, for medical or biological applications the details of both dimension and shape are important to the practice of the invention, as will be described in more detail below.

The distribution of nanoparticle shapes and dimensions or sizes that occur in any real collection of nanoparticles used in the practice of the invention must be taken into account. In a collection of nanoparticles the "most-probable" size is the nanoparticle size most likely to be found when an individual nanoparticle is selected from the mixture. For a metal particle to have absorption due to plasmon resonance, the particle size has to be greater than 1 nm to possess sufficient pool of electrons for collective (plasmon) resonance absorption. On the other hand, preferably, the most probable size of the particles of the contrast agents will be less than 3000 nm. This limitation comes from necessity for the particle to be administered and propagate through biological tissue, such as microscopic blood vessels and/or intercellular space. More preferably, the most-probable size of the particles will be less than 1000 nm. Still more preferably for certain applications that involve molecular targets, the most-probable size of the particles will be less than 100 mm. Thus, the invention encompasses any use of contrast agents for optoacoustic imaging comprising metal particles or aggregates of metal particles whose shape is matched to the wavelength of the imaging irradiation and whose size is less than 1000 nm, preferably less than 250 nm, and most preferably less than 100 nm but greater than 1 nm, and whose composition is made to enhance acoustic response to pulsed optical irradiation.

In an embodiment, the longest dimension of the most probable nanoparticles in a collection of nanoparticles is in the range from about 2 nanometers to about 200 nanometers. A collection of nanoparticles may have a plurality of size distribution modes. The term "nanoparticles" and "nanoparticulate" as used herein is not limited to particles having dimensions of 100 or less, but extends to the entire range from 1 nm to 3000 nm as stated. In practice of the invention, the largest dimension of the non-spherical particles will most preferably be less than 100 nm, within the more general classification of "nanoparticles."

A collection of particles has both a number-average weight and a weight-average weight. The number-average weight is $NW=\Sigma(n_j w_i)/\Sigma n_j$, where in any given sample $n_i$ is the number of particles having a particle weight $w_i$. The weight average is $WW=\Sigma(n_i w_i^2)/\Sigma(n_j w_j)$. When all particles have the same weight, NN and WW are equal. When there is a distribution of weights, NN is larger than WW. The ratio of the weight average to the number average is a useful measure of the range of particle weights and may be defined as the polydispersity index (PDI). For an ideal system, the PDI will be 1. The invention encompasses any use of contrast agents for optoacoustic imaging comprising metal particles or aggregates of metal particles whose shape is matched to the wavelength of the imaging irradiation and for which the ratio of the weight average of particle weights to the number average of particle weights is preferably less than 5, more preferably less than 2, and most preferably less than 1.2.

Photon correlation spectroscopy is commonly used to determine the mean particle size and size distribution of spherical colloidal particles with diameters between 5 nm and 3 microns, and can be used for a determination of the non-spherical nanoparticulates of this invention. However, the polydispersity index measured by photon correlation spectroscopy (PI) is a functional definition based on the decay properties of the autocorrelation function of the light scattering intensity. It ranges from 0 to 1 and is different from the PDI defined above. In the practice of the invention the PI measured by photon correlation spectroscopy of the metal particles will preferably be less than 0.5, more preferably less than 0.25, and most preferably less than 0.1. The invention encompasses any use of contrast agents for optoacoustic imaging comprising metal particles or aggregates of metal particles whose shape is matched to the wavelength of the imaging irradiation and for which the polydispersity index measured by photon correlation spectroscopy is less than 0.5, more preferably less than 0.25, and most preferably less than 0.1.

Composition

Metallic Particles

The term "metallic," as used to characterize the nanoparticulates used in this invention, means an electrically conductive material capable of plasmon-derived absorption of electromagnetic radiation. Such material has a negative value of the real part of the complex dielectric permeability. A "metallic" material therefore includes not only true metals but also carbon and other elements having a negative value of the real part of the complex dielectric permeability. Suitably the metal of a collection of at least partially metallic nanoparticles is selected from gold, silver, platinum, a form of carbon having metallic properties, a mixture of at least two of said metals, or an alloy of at least two of said metals.

The "at least partially metallic" nanoparticulate or nanoparticulates used in this invention may be solid (that is, composed of a single material having a negative value of the real part of the complex dielectric permeability or compound or alloy of such substance) or may comprise a shell. For a shell structure, the core may be metallic and the shell may be formed of a dielectric material. Alternatively, the shells may be metallic and the core may be a dielectric substance or may be a core substance having a coefficient of thermal expansion in the range of $9\times10-2$ mm$^3$/joule to $2\times103$ mm$^3$/joule. Suitably such a substance is selected from the group comprising water, aqueous gels, hydrogels, gases, lipids and other organic substances.

Thus the invention encompasses the use of nanoparticulate contrast agents comprising any metal, metal alloy, or combinations of metals and non-metals. The nanoparticulates can comprise a single metal, such as gold, or can be layered structures, such as silica shapes covered with gold shells. When the nanoparticulates comprise a single metal, gold, silver, palladium, and platinum are preferred. More preferred are gold and silver. Especially preferred is gold, for which the plasmon resonance occurs at exceptionally long wavelengths in comparison to most other metals.

Coated Metallic Particles

The invention encompasses the use of "bare" metal particles or aggregates of metal particles, that is, particles or aggregates of particles with no coating of organic or inorganic material. In general, however, it will be desirable that the particles have a coating to optimize the biological and chemical properties of the particles and to maximize the optoacoustic signal. The invention encompasses the use of coated metal particles or aggregates of metal particles as contrast agents for optoacoustic imaging.

The invention encompasses the use of contrast agents comprising both coatings that are covalently bound to the surface of the particles and coatings that physically adhere to the surface of the particle. The latter method of binding will generally be more preferred. The coating material may comprise any of the elements. However, coatings comprising carbon, oxygen, nitrogen, hydrogen, sulfur and phosphorous are preferred.

The surfaces of the bare metal particles are hydrophobic. A coating designed to stabilize a suspension of the particles in an aqueous solution should be ambiphilic, that is, it should have both hydrophobic and hydrophilic parts. Surfactants are an example of ambiphilic substances. The invention encompasses the use of polymeric or non-polymeric surfactants to stabilize the metal particles or aggregates of metal particles of the invention. Particularly desirable surfactants are block copolymers, especially block copolymers in which one block is poly(ethylene glycol) (PEG).

The invention encompasses the use of proteins or other biological molecules as surfactants. The invention further encompasses the use of chemically modified proteins or other biological molecules as surfactants.

One purpose of the surfactants or other substances used to coat the particles is to prevent particle aggregation. Aggregation of the individual particles would lead to particle growth and to precipitation of the particles from the suspension that would shorten the shelf life of any formulation for the contrast agents. The invention encompasses the use of contrast agents for optoacoustic imaging comprising metal particles or aggregates of metal particles that are stabilized against particle aggregation and precipitation through the use of surfactants or other particle coatings.

Another purpose of the surfactants or other coatings is to modify the blood lifetime of the particles. As a rule, particulate matter is taken up by macrophages in the body and is hence cleared by the RES. The use of derivatives of poly(ethylene glycol) (PEG) to lengthen the lifetime of particulate drug formulations is well known (Kumar, 2000). Stealth liposomes are examples of particulate materials in which PEG or a derivative of PEG serves to inhibit uptake of the particles by the RES. The invention further encompasses the use of contrast agents for optoacoustic imaging comprising metal particles or aggregates of metal particles that are stabilized against uptake by the RES by appropriate surfactants or other particle coatings.

Optionally, the surfactant may serve as a platform for the attachment of other chemical species with desirable biological or chemical properties. For this purpose, a surfactant or other surface-active agent with reactive functional groups is desirable. The types of reactive functional groups that are possible for the practice of this invention include, but are not limited to hydroxyl groups, thiol groups, amine groups, hydroxyl, halo, cyano groups, sulfhydryl, carboxyl, and carbonyl groups, as well as carbohydrate groups, vicinal diols, thioethers, 2aminoalcohols, 2-aminothiols, guanidinyl, imidazolyl and phenolic groups. The invention encompasses the use of contrast agents for optoacoustic imaging comprising metal particles or aggregates of metal particles that are stabilized against uptake by the RES surfactants with any reactive functional group suitable for the attachment of targeting vectors or other groups that modify the physical or chemical properties of the metal-particles.

Optionally, the surfactants or other coatings on the nanoparticles can be infused with a substance that undergoes a phase change at a temperature between 35° C. and 100° C. Desirable are substances that are water insoluble at temperatures below 100° C. Especially desirable are substances that are water insoluble and undergo a transition from a liquid or solid to a gas as the temperature rises from body temperature as energy is released through photon absorption by the particle. Examples of suitable substances for infusion into the particle coating are low-molecular weight hydrocarbons such as hexane and pentane, alcohols such as 1-pentanol and 1-hexanol, ketones such as dipropyl ketone, and other organic compounds. The invention encompasses the use of nanoparticulate contrast agents for optoacoustic imaging comprising surfactants infused with any compound that undergoes a phase transition between 35° C. and 100° C.

The general structural pattern for attachment of additional chemical species (here called MODIFIERS) to the surfactants is:

SURFACTANT-LINKER-SPACER-LINKER-MODIFIER

As a result, both the surfactant and the attachment should have reactive functional groups. The spacer, which is optional, should have a pair of reactive functional groups. The invention further encompasses the use of contrast agents for optoacoustic imaging comprising metal particles or aggregates of metal particles that are stabilized against uptake by the RES by appropriate surfactants or other particle coatings to which modifiers are attached through one or more linkers and an optional spacer.

The spacers may comprise links that are cleavable under the action of enzymes, acids, bases, and other chemical or biological entities. With such cleavable spacers, it will be possible for the contrast agent to have properties that change over time. For example, before cleavage of the spacer, the contrast agent may have a strong affinity for certain cells, organs, or disease lesions. After cleavage, it will rapidly be cleared from the body. The invention encompasses the use of nanoparticulate contrast agents for optoacoustic imaging comprising surfactants with modifiers attached directly or through linkers and spacers that are cleavable under the action of enzymes, bases, acids, or other chemical entities.

A particularly desirable modifier in the practice of the invention is a "targeting vector". A targeting vector is any chemical group or ligand that binds to a "targeting receptor" associated with the organ or lesion of interest. The targeting vector can be derived from any synthetic, semi-synthetic, or naturally occurring chemical species. Materials or substances that can serve as targeting vectors include amino acids, peptides, oligopeptides, polypeptides, proteins, antibodies, antibody fragments, hormones, hormone analogues, glycoproteins, lectins, sugars, saccharides, including monosaccharides and polysaccharides, carbohydrates, vitamins, steroids, steroid analogs, hormones, cofactors, and genetic material, including nucleosides, nucleotides, nucleotide acid constructs and polynucleotides and derivatives of these materials. The targeting vector can be either an independent molecule or a molecular fragment. The invention encompasses the use of contrast agents for optoacoustic imaging comprising metal particles or aggregates of metal particles to which one or more targeting vectors are attached, either through a chemical bond or through direct interaction with the particle surface.

Regardless of whether the targeting vectors adhere directly to the surface of the metal particle or is attached indirectly through the surfactant, the receptors for which the targeting vectors have a special affinity can be chemical groups, proteins, or other species that are overexpressed by cancerous tissue or cells. In general, terms the receptors can be any chemical feature of the organ or tissue type to be imaged. The receptors can also be independent chemical entities in the blood or other body fluids. Examples of such receptors are externally administered drugs, drug components, or drug metabolites. The invention encompasses the use of contrast agents for optoacoustic imaging comprising metal particles or aggregates of metal particles that are specifically modified to interact with receptor sites that are characteristic of cancerous cells, cancerous tumors, vascular systems, sites of infection, or sites of inflammation. Examples of receptors related to cancer cell genes include, but not limited to vascular endothelial growth factor, epidermal growth factor receptor, HER2/neu receptor, folate receptor, human milk fat protein, annexin-5, proliferating cellular nuclear antigen etc.

In an embodiment of the invention, the at least partially metallic nanoparticles in a collection of nanoparticles are at least partially coated with an inorganic dielectric material.

Electromagnetic Radiation

In accordance with the invention, a wavelength or wavelength spectrum of electromagnetic radiation is chosen to match the maximum of absorption for at least partially metallic non-spherical nanoparticles which may be at least partially coated with organic or inorganic dielectric material or conjugated with biological molecules.

The method of imaging encompassed by the invention can be performed with irradiation with electromagnetic irradiation of any frequency or wavelength to generate acoustic or pressure waves in the body. Wavelengths in the visible or infrared range from about 200 to about 3000 nm are preferred. More preferred is irradiation in the near-infrared wavelength range from 650 to 1200 nm. The irradiation can be generated with a laser, but the invention encompasses the use of any radiation source, regardless of whether it can be called a laser. Examples of alternative radiation sources include flash lamps, incandescent sources, klystrons, radioactive substances, etc. The invention encompasses the use of contrast agents for optoacoustic imaging comprising metal particles or aggregates of metal with electromagnetic irradiation of any wavelength, preferably a wavelength between 200 and 3000 nm, more preferably a wavelength between 650 and 1200 nm.

The selected wavelength or selected spread of wavelengths of electromagnetic radiation used in connection with at least partially metallic nanoparticles of formed shape for this invention is selected from the spectrum of wavelengths in the range from 3 nanometers to 300 millimeters. In an embodiment the wavelengths are in the visible and near infrared spectrum. Suitably the spectrum is in the wavelength range from 650 nanometers to 1150 nanometers. Advantageously, the nanoparticles comprise gold and the wavelength for irradiation is from about 520 nanometers to about 1120 nanometers.

In an embodiment, the wavelength for irradiation is from about 520 nanometers to about 1120 nanometers, and the nanoparticles in a collection are at least partially gold, are elongated in at least one dimension, and have a most probable aspect ratio of at least 2.0. In another embodiment, the wavelength for irradiation is from about 520 nanometers to about 1120 nanometers, the nanoparticles in a collection are at least partially gold, are elongated, and have a bimodal distribution of aspect ratios. In a particular for the latter embodiment, one local maximum in the distribution of aspect ratios is about 4 and the other local maximum in the distribution of aspect ratios is about 8. In a multimodal distribution of aspect ratios, the electromagnetic radiation comprises two or more wavelength spreads. In an example for a bimodal distribution of aspect ratios of elongate at least partially gold nanoparticles, one wavelength band is from about 690 nanometers to about 800 nanometers and another wavelength band is from about 800 nanometers to about 1150 nanometers.

The optoacoustic signal is produced through plasmon derived resonance absorption by conductive electrons in the nanoparticles used in the invention. Suitably, the electromagnetic radiation used is pulsed and is emitted from a pulsing laser. Alternatively, the electromagnetic radiation is a modulated continuous wave.

In an embodiment of the invention, interaction of nanoparticles with the object being detected produces a shift of the absorption maximum by the nanoparticles for the selected wavelength or spread of wavelengths.

The Body For Administration of Nanoparticulates

The body in which a specific object is detected in accordance with the detection method of this invention may be animate or inanimate and the specific object may be animate or inanimate. Thus, without limitation, in terms of medical significance, for example, the body may be an in vivo or in vitro specimen, and the object may be a molecule or a virus or bacterium. The body animate may be an animate human or non-human, and the object may be biological and comprise a specific tissue, cell, microorganism or molecule. For example, the object detected may be a tumor in an animate human or a physiologically operative molecule such as glucose, an enzyme, a protein receptor or a nucleic acid.

The invention will be especially useful with respect to medical imaging of a human or non-human body. However, various other uses for the invention are also anticipated. For example, the method will be useful for the sensitive detection of environmental pathogens, such as harmful bacteria, spores of harmful biological agents, or viruses. When a suspected pathogen is examined, it will generally be sufficient that the test sample simply be bathed in the formulation containing the contrast agent.

Administration

For imaging of a human or a non-human body, many modes of application are possible, depending on the imaging requirements. Administration of the contrast agent can be systemic or local. Administration can be made intravenously, orally, topically or through direct application of the agent to human or non-human tissue or cells.

In an embodiment of the invention, the metal particles or aggregates of metal particles are entrapped in lipid vesicles or liposomes. As known in the art, liposomes are vesicles made from phospholipids defining a lipid phase encapsulating an aqueous phase. The liposomes can be prepared from a phospholipid, such as, for example, dipalmitoylphosphatidylglycerol (DPPG) and dipalmitoylphosphatidylcholine (DPPC). The lipid wall can be strengthened when needed by the use of cholesterol in the lipid phase to prevent leakage of the lipid wall. The phospholipids used to encapsulate the dye can have a transition temperature below 37° C., such as phosphatidyl choline. The liposomes can themselves comprise one or more targeting vectors. Thus, the invention encompasses optoacoustic imaging with contrast agents comprising metal particles or aggregates of metal particles whose shape is tuned to the radiation wavelength for the imaging and which are enclosed in liposomal vesicles or other closed vesicular structures.

Optionally, the lipid wall of liposomes used in the practice of the can be infused with a substance that undergoes a phase change at a temperature between 35 C and 100° C. Desirable are substances that are water insoluble at temperatures below 100° C. Especially desirable are substances that are water insoluble and undergo a transition from a liquid or solid to a gas as the temperature rises from body temperature as energy is released through photon absorption by the particle. Examples of suitable substances for infusion into the lipid bilayer are low-molecular weight hydrocarbons such as hexane and pentane, alcohols such as 1-pentanol and 1-hexanol, ketones such as dipropyl ketone, and other organic compounds. The invention encompasses the use metal particles or aggregates of metal particles are entrapped in lipid vesicles or liposomes infused with any compound that undergoes a phase transition between 35° C. and 100° C. for optoacoustic imaging.

In general, the particulate portion of the contrast agent will be dispersed in a sterile carrier liquid, which can be water, a water solution such as saline solution, an organic liquid, or an oil, including oils of animal, mineral or synthetic origin. Furthermore, the formulations used for practice of the invention can include a variety of excipients such as one or more neutral lipids, charged lipids, gases, gaseous precursors, liquids, oils, diagnostic agents, targeting ligands and/or bioactive agents. The formulation can also comprise stabilizers to slow the chemical degradation of the components.

In one embodiment of the invention, the contrast agents are administered in conjunction with the use of hyperthermia, that is, the artificial elevation of the local temperature of an organ or another body part. Kong, et al. (2000 and 2001) teach, that hyperthermia accelerates the passage of nanoparticles through the capillaries of the vascular system of growing tumors. Hyperthermia will also enhance the uptake of the contrast agent of other types of diseased tissue, sites of inflammation caused by infection or trauma.

The present invention further anticipates the use of a contrast agent for optoacoustic imaging in conjunction with therapy. Therefore, the composition can contain adsorbed drugs, pro-drugs, or other therapeutic agents such as light-absorbing compounds useful in photodynamic therapy.

In a particular application of the invention, the method includes generating an image of an object in an animate human or non-human animal body or part thereof and comprises: (a) administering to the animate body a physiologically tolerable contrast agent comprising a collection of at least partially metallic nanoparticles having (i) a most probable size no smaller than about 1 nanometer and no larger than about 1000 nanometer and (ii) a formed shape capable of absorbing specific selected wavelengths of electromagnetic radiation, (b) exposing the animate body or part thereof to electromagnetic radiation in the near-infrared range of wavelength spectrum having a selected wavelength or spread of wavelengths larger by a factor of at least 3 relative to the minimal size of said nanoparticles, (c) detecting a optoacoustic signal generated in said body as a result of heating said collection of at least partially metallic nanoparticles, and (d) generating an image from said detected signal. Suitably the optoacoustic signal is converted into an electronic signal using a detector selected from thermal, acoustic, optical or infrared detectors or a combination of one or more of such detectors which is used to generate the image. The nanoparticles collect at the object, and the image provides visual information about the detected object.

In a further aspect of the invention, a tumor of an animate human or non-human animal body or part thereof is non-invasively detected and treated to destroy the viability of the tumor. This aspect, for treating the tumor, comprises (a) administering to the body or a part thereof in a manner to position where presence of a tumor is to be examined a physiologically tolerable contrast agent comprising a collection of at least partially metallic nanoparticles having a most probable size no smaller than about 1 nanometers and no larger than about 1000 nanometers and a formed shape capable of absorbing specific selected wavelengths of electromagnetic radiation, (b) exposing the body or part thereof to electromagnetic radiation in the near-infrared range of wavelength spectrum having a selected wavelength or spread of wavelengths larger by a factor of at least 3 relative to the minimal size of the nanoparticles, (c) detecting a optoacoustic signal generated in the body as a result of heating the collection of at least partially metallic nanoparticles, (d) converting the optoacoustic signal into an electronic signal characterized by at least one parameter selected from amplitude, frequency, phase, temporal profile, time of arrival, frequency spectrum, or a combination of any one or more thereof, (e) presenting the signal for assessment of the at least one parameter by a human or a machine for whether a tumor is present in the body, and (f) directing onto the nanoparticles a selected wavelength or spread of wavelengths not absorbed by water to heat the nanoparticles at the tumor and raise the temperature of the tumor sufficiently to destroy viability of the tumor.

DESCRIPTION OF DRAWINGS

FIGS. 11B-11C demonstrate the high sensitivity of optoacoustic detection (a concentration about 1 picomole per liter was detected with signal-to-noise ratio of 2).

DETAILED DESCRIPTION OF THE INVENTION

Figure 1:
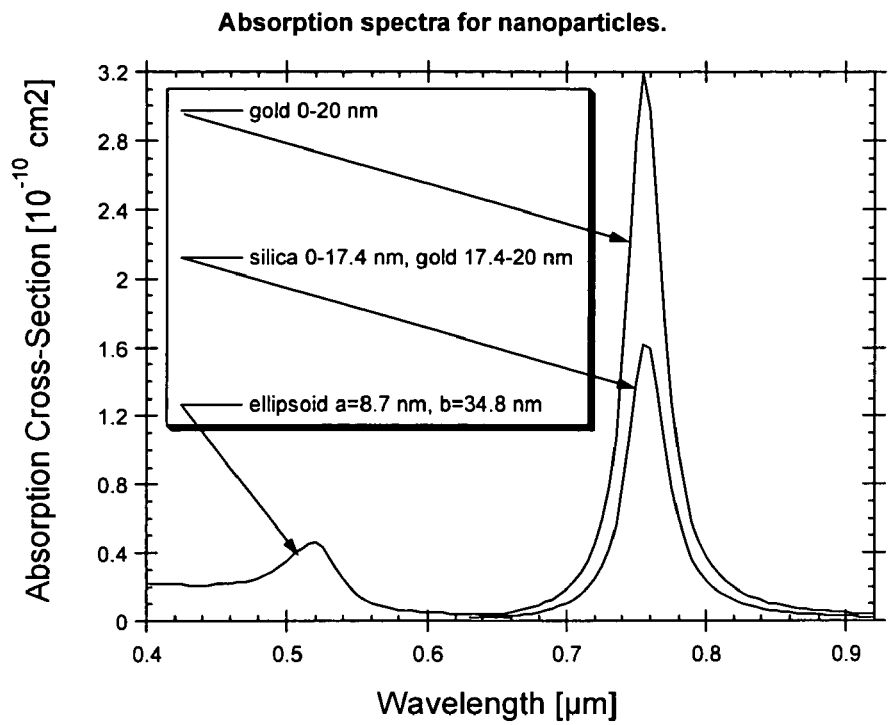
FIG. 1. Optical absorption cross-section for gold nanoparticles with equal volume of 33493 $nm^3$. Prolate nanoparticles possess greater absorption coefficient compared with spherical nanoparticles and their absorption peak is narrower FIG. 2. Molar extinction coefficient in [$cm^{-1}$] for gold nanorods and ellipsoids of revolution as a function of optical irradiation wavelength [μm]. The curves almost fully match having minimal deviation from each other.

The invention is a method for optoacoustic imaging with the help of contrast agents comprising non-spherical metal nanoparticulates. The optical properties of the metal nanoparticulates are "tuned" to maximize the absorption of light and the generation of the optoacoustic signal at the irradiation wavelength used for the imaging through control of the shape, composition and dimensions of the nanoparticulates.

The invention encompasses the use of contrast agents for optoacoustic imaging comprising metal nanoparticulates in which the shape, composition, and dimensions of the particles are chosen for maximal absorption of the radiation used for optoacoustic imaging. Preferably, the choice of the shape, composition, and dimensions of the particles will place the absorption maximum of the particles near the irradiation wavelength. More preferably, the choice of the shape, composition, and dimensions of the particles will place the absorption maximum of the particles near the irradiation wavelength and will maximize the absorption for light absorption at that wavelength.

In this invention, sensitivity and contrast in an optoacoustic image are enhanced by the use of contrast agents comprising metal particles whose optical properties are "tuned" to the wavelength of the exciting radiation for the optoacoustic imaging through the shape, composition, and dimensions of the metal particles. In the practice of the invention, the shape, composition, and dimensions of the metal particles may, in addition, optimize the acoustic response of the metal particles to pulsed electromagnetic radiation. The contrast agents can comprise surface-active agents or surfactants on the surfaces of the metal particles, as well as substances to modify the chemical and physical properties of the metal particles ("modifiers"), which can themselves be surfactants and interact directly with the metal particles or can be attached to or otherwise interact with the surface-active agents or surfactants. The modifiers can be "targeting vectors" to enhance the affinity of the contrast agents for certain receptor sites specific to the organs, tissues, or disease lesions of interest or to chemical substances contained in the fluids of the organs, tissues, or disease lesions. The modifiers can also serve to slow the clearance in the body of the metal particles. The invention anticipates the use of the contrast agents as part of a formulation that can comprise various other excipients and drug stabilizers.

Particles

In the general case, the metal particles will be represented by three classes. The first class of particle shapes comprise solid elongated particles such as prolate ellipsoids; oblate solids; and rods, including cylindrical rods and non-cylindrical rods (round particles with axial symmetry) and parallelpipeds and pyramids (polyhedra, particles having a number of flat surfaces and corners). Cylindrical rods are rods for which all of the cross sections along one of the axes in three-dimensional space are circles. Non-cylindrical rods are elongated shapes for which all of the cross sections along one of the axes in three-dimensional space are equivalent non-circles. Generally, the metal particles will have an elongate shape, i.e., they have any geometrical shape in which one dimension is longer than the other two dimensions in three-dimensional space. The second class of particle shapes that can be useful in optoacoustic applications is a class of polyhedra shells. The shells can be either cubes, hollow metal or metal filled with dielectric or metal covered with dielectric. Particles with corners, such as solid parallelpipeds and hollow boxes, pyramids, cones etc. may be used. The new application of these particles is in optoacoustic (optoacoustic) detection and imaging.

The invention encompasses the use of particulate contrast agents comprising any metal, metal alloy, or combinations of metals and non-metals. The nanoparticles can comprise a single metal, such as gold, or can be layered structures, such as silica rods covered with gold shells. When the particles comprise a single metal, gold and silver are preferred. Even more preferred is gold, especially for applications related to detection in the depth of optically turbid medium, such as tissue. For gold, the plasmon resonance occurs at exceptionally long wavelengths in the visible spectral range in comparison to most other metals.

The invention encompasses the use of nanoparticles made of carbon nanotubes. Surprisingly, we found that carbon nanotubes possess exceptionally strong ultrasonic (pressure) response to pulsed laser irradiation in the near-infrared spectral range. The laser-induced pressure pulses from a mixture of carbon nanotubes was significantly stronger than that from a solution of dye with similar optical absorption. Based on our preliminary studies, we believe that single wall carbon nanotubes with metallic properties will be the most preferable as optoacoustic (optoacoustic) contrast agent. However, based on our finding, it would not surprising to one skilled in the art that multi-walled carbon nanotubes with various structures also can possess strong pressure response to pulsed electromagnetic radiation and thus, can be used as signal-enhancing agents in optoacoustic (optoacoustic) systems.

The particles used in the practice of the invention may either be solids, that is, they can be composed of a single metal, or they can be metal shells filled with another substance. Preferred substances will have exceptionally large thermal coefficients of expansion. Examples of substances that can be contained in metal shells for the practice of the invention are water, gases such as nitrogen, argon, and neon, aqueous gels, such as polyacrylamide gels and gels containing gelatin, and organic substances such as ethanol. Preferred fillers for metal shells are lipids, long-chain fatty acids, organic hydrocarbons, and other organic compounds comprising straight-chain hydrocarbon chains of 14 or more carbon atoms. Those skilled in the art will recognize many other substances that can be used as fillers in the practice of the invention.

The shape of the particles is more critical in the matching of the wavelength of irradiation than is the size of the particles. However, the particles must be smaller than the wavelength of the radiation. Furthermore, the size of the particles is crucial in controlling the biological properties of the particles, especially the bio-distribution and the blood clearance rate. For biological reasons, smaller particles will generally by favored over larger particles. However, particle sizes large enough to scatter light will be useful for distributing the radiation internally in tissue. Ultimately, there will be a compromise between possible particle sizes.

There are two main reasons why this invention teaches that elongated solid nanoparticles, shells and elongated shells will be the most useful as optoacoustic contrast agents. First, said particles absorb electromagnetic radiation with maximum absorption at a wavelength significantly shifted towards longer wavelengths range compared with the wavelength of spherically shaped particles of the same total volume, composition and otherwise identical to said non-spherical particles. Secondly, said particles absorb electromagnetic radiation stronger than spherically shaped particles of the same total volume and otherwise identical to the disclosed non-spherical particles.

In a typical formulation of the contrast agent used for practice of the invention, there will be a distribution of particle sizes. The "most-probable" size is the particle size most likely to be found when an individual particle is selected from the mixture and is discussed above under Summary of the Invention in connection with average weight, number-average and the weight-average molecular weights. In the practice of this invention, the ratio of the weight average of the particle weights to the number average of the particle weights will preferably be less than 10, regardless of the method of measurement of the particle weights. More preferably, it will be less than 5 regardless of the method of measurement of the particle weights. Most preferably, it will be less than 1.2. Experimentally, it may not always be possible to determine directly either the number average or the weight average of the particle weights. Methods such as gel permeation chromatography or size-exclusion chromatography separate particles based on size rather than weight. With proper calibration of the results, it is possible to relate the particle size to the particle weight, but the analysis is complicated when the particles have a non-spherical shape. Many characterization methods provide only a single moment of the complete distribution of weights. The use of photon spectroscopy to determine the mean particle size and size distribution is also described above under the Summary of the Invention. In the practice of the invention the PI measured by photon correlation spectroscopy of the metal particles will preferably be less than 0.5, more preferably less than 0.25, and most preferably less than 0.1.

A preferred shape is a cylindrical rod. For metal rods, the aspect ratio, that is the ratio of the length of a rod to its diameter, is the critical parameter controlling the match to the wavelength of irradiation. For gold rods, data published by Link and EI-Sayed, 1999 allows determination of the optimal aspect ratio. For irradiation at 600 nm, the optimal ratio is 2.0; for 650 nm, it 2.5; for 700 nm, it is 3.0; for 750 nm, it is 3.5; and for 800 nm, it is 4.0. Those skilled in the art will immediately recognize that this information is readily extrapolated and interpolated for other wavelengths.

As is the case for the particle weights, there will generally be a range of aspect ratios for the metal rods. The "most-probable" aspect ratio is the aspect ratio most likely to be found when an individual particle is selected from the mixture. The usefulness of the ratio of the weight-average to the number-average aspect ratios for measure of the width of the aspect ratio distribution is described above under the Summary of the Invention. For irradiation at 760 nm, the most-probable aspect ratio of gold cylindrical particles used in the practice of the invention preferably will be between 3.5 and 4.0. More preferably, the most-probable aspect ratio will be 3.5 and 3.7.

An effective method for measuring the number-average and weight-average aspect ratios is detailed analysis of an image from transmission and scanning electron microscopy. For the analysis, the solvent is stripped from the particles so that they are deposited unchanged on a surface (dry-drop method). The shapes and sizes of the particles in a representative region of the surface are then tabulated and the number average and weight average of the particle sizes and aspect ratios are calculated. The invention anticipates that alternative methods of measuring the average aspect ratios will be available.

A useful alternative method of determining particle shape is based on the optical spectrum. In each case the spectrum of an ideal collection of particles with uniform shape, composition, and dimensions can be readily calculated based on the well-known Mie-Gans theory. As previously mentioned, for a given composition the particle shape affects the absorption spectrum much more strongly than does the particle size. Therefore, computer fitting of the experimental spectra for actual collections of metal particles in terms of the spectra for metal particles of a range of shapes then provides the distribution of particle shapes. From the calculated distribution of particle shapes, the number average and weight average of the particle sizes can then be determined.

The invention anticipates the use of contrast agents sensitive to two different irradiation wavelengths. In this case, the contrast agent will comprise particles with two different aspect ratios. For example, the shape, composition, and dimensions of one type of nanoparticle in the mixture will be chosen to match the wavelength of 757 nm. This wavelength is emitted by an alexandrite laser and is especially useful for detecting vascular tumors rich in hypoxic blood. The shape, composition, and dimensions of the second type of nanoparticle in the mixture will be chosen to match the wavelength of 1100 nm. This wavelength is highly penetrating and is especially sensitive to tumors and other tissues containing deoxygenated blood. Comparison of the images obtained with a contrast agent containing a mixture of particle sizes will be a powerful method for differentiation between diseased tissue and either normal tissue or abnormal, but harmless, tissue.

Methods for the preparation of colloidal suspensions of gold nanoparticles are well known. The use of spherical particles in non-spherical nanoparticulate aggregates of this invention has been described. Spherical particles can readily be prepared by the chemical reduction of tetrachloroauric acid (Beesley, 1989). Various chemical agents and biological molecules readily adhere to the surface of these spheres (Beesley, 1989, Hayat, 19889). Colloidal suspensions of spherical gold particles with adsorbed antibodies were described by Hainfeld, 1995 and by others (Beesley, 1989, Hayat, 1989).

Spherical gold nanoparticles may be produced by a procedure that follows Hayat. A mixture of 1 ml of a solution of 1 mg tetrahydrochloroauric acid (AuCl3) in 100 ml distilled water and 50 ml distilled water is brought to boil with constant stirring. To this is added 0.5-5.0 ml of a solution of 1 mg of trisodium citrate in 100 ml of distilled water. The boiling is continued for 5 min, during which time (after 20-30 sec) the solution turns purple due to the formation of the colloidal gold. At the end of the reaction period, the liquid is cooled under running water. The pH should be about 5.0. Different sizes can be produced through variation in the amount of citric acid used. When the preparation is carried out with 1 ml of the citric acid solution, the particle size will be about 36 nm, and the polydispersity index (PI) measured by photon correlation spectroscopy will be about 0.35. Optional stabilization of the colloidal suspension against particle aggregation and precipitation is accomplished by addition of 4 g/l of Poloxamer 188 to the final solution. Comparable amounts of other polymeric surfactants will also be sufficient for stabilization.

Various methods for the preparation of non-spherical gold particles have also been reported. Preparation of nanorods in a matrix yields particles with a narrow distribution of sizes and shapes (Sandrock et al., 1999). The aluminum oxide can be dissolved to release the gold particles through treatment with base (van der Zande et al., 1997).

A procedure for gold deposition into a porous aluminum oxide membrane, followed by release of the particles from the matrix follows van der Zande et al. and Sandrock et al., as follows.

Stainless steel coils connected to an external refrigeration circulation bath maintaining a 1:1 mixture of ethylene glycol and water at 0° C. are placed in a two-electrode anodization cell. Lead foil (6.5×14×0.2 cm) serves as the cathode and a polished plate of aluminum (10×10 cm) serves as the anode. The electrolyte is 6% sulfuric acid. A film of aluminum oxide with a pore size of 32 nm and a thickness of 40 to 60 microns develops after 14 h with application of a cell potential of 20 V. The potential is reduced gradually from 20 V to 2 V over a period of 1.5 hr. At each reduction step the potential is allowed to rise to 85% of the former value before it is reduced further. The film is then released from the aluminum plate by immersion of the plate in a 25% solution of sulfuric acid for about 3 hr. The films are then rinsed with deionized water, ethanol, and acetone and are then air-dried. If desired, the films can be briefly treated with 1.25 M NaOH to widen the pore size. The barrier side of the film is sputtered with about 45 nm of silver with a plasma deposition device. The silver-coated film is then attached to a three-electrode cell equipped with an Ag/AgCl reference electrode and a platinum-mesh counter electrode. A foundation of 0.80 to 1.27 C/cm² is deposited from a silver thiocyanate plating solution with application of −0.6V vs. a Ag/AgCl electrode. After the film is rinsed with deionized water, gold nanoparticles are deposited in the pores from gold plating solution (Technic Inc.) with application of a potential of −0.9 V vs. Ag/AgCl. The length of time for the deposition determines the length of the particles.

The oxide film with gold encapsulated in the pores is then immersed in nitric acid to dissolve silver on the surface of the film and in the pores. The films containing gold alone are then rinsed with water, ethanol and acetone and allowed to dry in the air. The aluminum oxide matrix is then dissolved in 1.25 M NaOH containing 4 g/l Poloxamer 188. The pH of the solution brought to neutral pH through titration with 3 N HCl.

A procedure for preparation of gold nanorods by gold deposition in a polycarbonate matrix follows van der Zande-1997. Copper is deposited on one side of the polycarbonate from a 0.01 M solution copper (II) sulfate by application of a constant voltage of −0.05 V vs. a standard calomel electrode for 100 s. After washing of the film with ultra pure water, any remaining copper ions are removed by a second electrodeposition step with a 0.01 M H2SO4 solution and application of a potential of −0.2 V vs. a standard calomel electrode for 100 s. Gold is deposited from a 0.32 M solution of gold (I) cyanide containing 0.26 M citric acid and 0.65 M KOH under a constant voltage of −1.00 V until the final pH is between 5 and 6. The copper is selectively dissolved by treatment of the membrane for 30 min with a copper etching solution made from 25 ml/l of 98% sulfuric acid, 75 ml/l hydrogen peroxide and a few drops of 85% phosphoric acid, then diluted 100 fold. The polycarbonate is then dissolved with a solution of 0.026 g/ml of Poloxamer 188 in methylene chloride to leave the stabilized particles as a methylene chloride suspension. Extraction into water leaves an aqueous suspension of the particles.

Wang and coworkers, followed by El-Sayed and coworkers, have discovered that electrochemical production of gold particles into a "shape-inducing" reagent results in gold rods of uniform shape and size (Yu et al., 1997, Mohammed, 1998). A procedure for prearation of gold nanorods using electrochemistry follows Yu et al. and Mohamed et al. A simple two-electrode electrochemical cell is set up with a gold plate (3×1×0.05 cm) as the anode and a platinum plate (3×1 0.5 cm) as the cathode. Both electrodes are then immersed in an aqueous solution of hexadecyltrimethylammonium bromide and tetraoctylammonium bromide. Small amounts of acetone and silver nitrate are added to facilitate the formation of the rods. The transfer of gold from the gold plate to the nanoparticles takes place upon the application of a controlled current of 3-5 mA for 30-45 min with ultrasonification at 38° C. The ammonium salts used in the preparation already stabilize the rods produced by this method. Additional stabilization may be accomplished by the addition of a polymeric surfactant such as Poloxamer 188. The appropriate concentration of Poloxamer 188 can be determined by experimentation. From the suspension of naked gold particles, 10 aliquots of 0.5 ml are removed. To each of these is added an aliquot of a different concentration of the Poloxamer solution. After the solutions of the Poloxamer and the gold particles have been allowed to sit for 1 min, 0.1 ml of 10% NaCl solution is added to each with agitation. The solution with the least amount of Poloxamer that does not change color from red to blue is selected. The Poloxamer concentration of this solution is the least sufficient for particle stabilization. A similar procedure will be appropriate for choosing the appropriate concentration of other stabilizers.

Kameo et al. teach that photochemical reduction of gold solutions in the presence of alkyltrimethylammonium chlorides of varying chain lengths leads to gold fibers of length determined by the alkyl chain length. A procedure for preparation of gold nanorods using photochemistry and following Kim-2002 is as follows. To an aqueous solution of 3 mL of 0.08 M hexadecyltrimethylammonium bromide and 0.42 mg/mL tetradodecylammonium bromide is added 0.25 mL of 0.024 M $HAuCl_4 3H_2O$, 0.065 mL acetone, 0.045 mL cyclohexane, and 31.5 mL of 0.01 M silver nitrate solution. The combined solution is then irradiated with at a wavelength of 254 nm (420 microW/cm²) for about 30 h. The product is centrifuged at 3000 rpm for about 10 min. The supernatant is collected and centrifuged at 10000 rpm for 10 min. The precipitates from both centrifugations are collected, combined, and redispersed in deionized water. The mean aspect ratio of the dispersed gold nanoparticles will be about 4.8. Additional stabilization of the gold nanoparticles produced by this method may be accomplished by the addition of a polymeric surfactant such as Poloxamer 188 to the final suspension as is described in Example V.

Recently, Xia has reported fabrication of cube-shaped nanoparticles of silver and gold with a simple wet chemical reduction process. With the aid of the silver nanocubes, hollow gold nanoboxes could be produced (Sun Y, Xia Y. "Shape-controlled synthesis of gold and silver nanoparticles", Science, 2002; 298(5601): 2176-2179).

The invention anticipates that many other procedures for preparation of non-spherical metal particles, especially gold particles, will be available. These include production of particles in electric and/or magnetic fields, liquid crystals, and other ordering and orienting environments. The invention encompasses the use of non-spherical particles as contrast agents for optoacoustic imaging regardless of the method of preparation.

Methods for organizing metal nanoparticles into stabilized aggregates are known. Storhof et al., 2000 teach that covering the surface of different gold particles with complementary strands of DNA favors the self-assembly of the particles into ordered aggregates. Aggregate formation results from the favorable interaction between the complementary strands of DNA. The invention further encompasses the use of contrast agents for optoacoustic imaging comprising aggregates of spherical or non-spherical metal particles.

The generalized chemical structure of the surfactants of the invention plus a modifier is: SURFACTANT-LINKER-SPACER-LINKER-MODIFIER Where the linkers can themselves be a chemical functional group in the surfactant or can be individual chemical entities and where both the linkers and the spacers are optional. The above structure is representative of the general nature that a chemical link between the modifier and the surfactant might take, but is not intended to be limiting as to other means of binding the modifier to the surfactants. It should also be recognized that each surfactant molecule can have attached more than one molecule of a modifier, and that each surfactant molecule can have attached more than one type of modifier. In one embodiment of the contrast agents of the invention, the modifier molecules interact with the surfactants without formation of covalent chemical bonds.

The nature of the particles is described above and in the examples below. The following paragraphs describe in detail the nature of the surface-active agents or surfactants, the linkers or linking groups, the spacers, and the modifiers.

Surfactants

The invention encompasses the use of "bare" metal particles or aggregates of metal particles, that is, particles or aggregates of particles with no coating of organic or inorganic material. In general, however, it will be desirable that the particles have a coating to modify the biological and chemical properties of the particles.

Metal particles coated with dielectric materials, such as protein, also can change optical properties. As shown in the Example XIV, a protein (dielectric) shell on the surface of a gold (metal) nanoparticle shifts maximum of optical absorption significantly into near-infrared spectral range. This shift is the most pronounced in thin dielectric layers (shells) and saturates with increased thickness. Such a behavior makes this effect truly practical: if a metal particles is covered only by a thin layer of protein, the effect of red-shift will be substantial (measurable).

Stabilization of colloidal suspensions of metal particles will generally require that the particles be treated with a surface-active agent or surfactant. The surface of a gold particle is hydrophobic. Stabilizing the particles in aqueous will generally require coating the particles with an ambiphilic molecule, a molecule with both hydrophobic and hydrophilic parts. Surfactants are an example of ambiphilic substances. However, the invention encompasses the stabilization of the particles with any type of chemical species that both adheres to the metal particles and interacts positively with water, whether or not such substance is generally considered a surfactant. Appropriate surface-active agents are also known as wetting agents, solubilizing agents, or emulsifying agents. The coating material can comprise any of the elements. However, coating comprising carbon, oxygen, nitrogen, hydrogen, sulfur and phosphorous are preferred. In one embodiment of the invention, the surface-active agent is a protein or other biological molecule or a chemically modified protein or other biological molecule.

Optionally the surfactants will contain functional groups form coordinate bonds with gold atoms on the particle surfaces. Examples of functional groups that can form coordinate bonds with metal atoms are carbon-carbon double bonds, carbon-carbon triple bonds, cyano groups, amino groups and other functional groups containing nitrogen, phosphine groups and other phosphorous groups containing phosphorous, hydroxyl and other functional groups containing oxygen, and mercapto groups and other functional groups containing sulfur.

Block copolymers in which one or more sections are chains of poly(ethylene glycols) (PEG) are especially desirable as surfactants in the practice of the invention. PEG's are simple, neutral polyethers whose properties have been given much attention in biotechnical and biomedical applications (see, for example, J. Harris, 1992, Kumar, 2000). They are soluble in organic solvents and are highly hydrated in aqueous environments, with two or three water molecules bound to each ethylene glycol segment.

PEG's are known to be nontoxic and harmless to proteins or cells. They are readily modified and covalently bound to other molecules, with only little effect on their chemistry. PEG chains covalently linked to other molecules or to other polymeric chains are known to be non-immunogenic and non-antigenic. The invention anticipates the use of PEG systems with attached targeting vectors and other modifiers as surfactants.

The high degree of aquation of the PEG chains has the effect of inhibiting the adsorption of other polymers and proteins onto a PEG-modified surface. Stealth liposomes are examples of particulates materials in which PEG, or a derivative of PEG serves to inhibit update of the particles by the RES.

Slowing the clearance of particulate materials administered by intravascular injection is essential when those materials are targeted (actively or passively) to specific types of organs or lesions such as cancerous tumors. Rapid clearance of the agent from the blood prevents binding of the agent to the receptor sites by removing the agent before it ever reaches those sites. Of course, slowing the short-term blood clearance of the agent has to be balanced against the preferable property that the agent is completely cleared from the body in the long term. For most types of contrast agents, clearance of the contrast agents from normal tissues such as the liver, kidney and brain within a reasonable period of time is essential to minimization of the long-term toxicity of the agent.

The major mechanism for uptake of particles by the reticuloendothelial system (RES) is opsonization by plasma proteins in blood. The biological properties of PEG spacer elements used in accordance with the invention can serve to increase contrast agent circulation time in a similar manner to that observed for PEGylated liposomes (Klibanov 1990, Blume et al. 1990).

The invention encompasses the synthesis of surfactants with attached modifiers for coating the metal particles. These modifiers will control the chemical and biological properties of the particles.

The attachment of modifiers will occur through reactive functional groups on the surfactants. In this situation, the reactive molecules to which the modifiers are to be attached can be considered "precursor surfactants." The invention anticipates the possibility that the precursor surfactants can not actually act as surfactants but will require the attachment of the modifiers in order to become active.

The reactive groups can be located anywhere in the precursor surfactant molecule. However, for linear, polymeric surfactants, the reactive groups will most advantageously be located at the ends of chains. For branched polymeric surfactant, the reactive groups will most advantageously be located at the ends of chain branches.

The types of reactive groups that are possible for the practice of this invention include, but are not limited to hydroxyl, thiol, amine, halo, cyano, sulfhydryl, carboxyl, and carbonyl groups, as well as functional groups containing two or more reactive sites, such as carbohydrate groups, vicinal diols, thioethers, 2-aminoalcohols, 2-aminothiols, guanidinyl, imidazolyl and phenolic groups. Those skilled in the art will recognize that a wide variety of other reactive groups are possible, extensive examples of which are given in U.S. Pat. Nos. 6,123,923; 6,264,914 and 6,331,289, which are hereby incorporated by reference.

Various surfactants that are GRAS (generally accepted as safe) are available. For substances to be administered by intravascular injection, these include lecithin, Tween 80, Poloxamer 188 and sodium glycholate. It is highly likely that many other GRAS materials will become available in the future.

Tween 80 has the chemical formula polyoxyethylene sorbitan monolaurate. Poloxamers are available from BASF under the Pluronic® trade name. They are synthetic block copolymers of ethylene oxide and propylene oxide with the general formula $HO(C_2H_4O)_a(C_3H_6O)_b(C_2H_4O)_aH$.

It is significant that the hydroxyl end group at the end of the Pluronic® chain is a reactive group of the type described above. A reactive linker forming an ester with the hydroxyl group can be used for attachment of a modifier to the surfactant. Furthermore, the hydroxyl can be converted into other reactive groups for reaction with other types of linkers. Examples of alternative reactive groups to which the hydroxyl groups can readily be transformed by methods well known to those skilled in the art are halides and amine groups. Copolymers of poly(oxyethylene) and poly(oxypropylene) with amine chain ends are commercially available and have been used to stabilize colloidal gold particles (Gregoriadis and McCormack, 1998).

It is possible to obtain molecules that bind specifically to the surface of the metal particles by direct screening of molecular libraries for metal-binding molecules. For example, phage libraries displaying small peptides could be used for such selection. The selection can be made by simply mixing the metal particles and the phage display library and eluting the phages that bind to the floating microspheres. If desired, the selection can be done under "physiological conditions" (e.g. in blood) to eliminate peptides that cross-react with blood components. Binding moieties identified in this way can be coupled (chemically via peptide synthesis, or at the DNA-level with recombinant vectors) to a vector molecule, constituting a general tool for attaching any vector molecule to the microspheres.

Those skilled in the art will recognize that the surface-active agents of the present invention can also have other desirable biological or chemical properties. Especially desirable are surface-active agents that also act as "targeting vectors," that is, they have a special affinity for chemical or physical interaction with receptor sites characteristic to organs or disease lesions of interest.

Unusually high optoacoustic contrast will be achieved with the use of nanoparticles coated with surfactants that will become sufficiently heated when the nanoparticles absorb radiation to undergo a phase transition into the gaseous phase on the surface of the nanoparticle. Optionally, the surfactants or other coatings on the nanoparticles can be infused with a substance that undergoes a phase change at a temperature between 35° C. and 100° C. Desirable are substances that are water insoluble at temperatures below 100° C. Especially desirable are substances that are water insoluble and undergo a transition from a liquid or solid to a gas as the temperature rises from body temperature as energy is released through photon absorption by the particle. Examples of suitable substances for infusion into the particle coating are low-molecular weight hydrocarbons such as hexane and pentane, alcohols such as 1-pentanol and 1-hexanol, ketones such as dipropyl ketone, and other organic compounds.

Linkers

Most commonly, linkers (also called linking agents) will comprise two or more reactive functional groups, optionally connected by a spacer element. The bifunctional or polyfunctional linkers will react with specific functional groups within a molecule or between two different molecules, resulting in a bond between two parts of a molecule or a bond between two different molecular fragments.

In the context of the present invention, linkers will be especially useful for the attachment of targeting vectors to "precursor surfactants." Alternatively, or in addition, the links can serve to attach other types of modifiers to the surfactants. The precursor surfactants are molecules that may or may not be surfactants, that is they may or may not interact with the surface of a metal particle prior to attachment of the modifiers, but which do interact with the surface of a metal particle after attachment of the modifiers. In the practice of this invention, the surfactants with the attached modifiers will stabilize the particles against precipitation and/or aggregation. Attaching the modifiers to the precursor surfactants to form the surfactant actually used to stabilize the metal particles effectively serves as a mechanism for attachment of the modifiers to the metal particles.

The reactive functional groups in a bifunctional or polyfunctional linker or linking agent can be the same (homofunctional agents) or different (heterofunctional) agents. Thus, there is a diversity of potential reagents that can be used to bring about covalent bonding of chemical species, either intramolecularly or intermolecularly.

Those skilled in the art will recognize that a great variety of reactive functional groups can be incorporated into a linker. In general, the identity of the linker will be determined in part by the identity of the reactive functional groups to which the linker will attach.

Linker or linking agents suitable for linking chemical species with a wide variety of reactive groups are well known to those skilled in the art and are described in detail in U.S. Pat. Nos. 6,123,923; 6,264,914 and 6,331,289, which are hereby incorporated by reference. Representative examples of linker group are described below. Those skilled in the art will recognize many other possibilities.

Examples of reactive functional groups that will make a linker capable of reaction with sulfhydryl groups include $\alpha$-haloacetyl compounds of the type X—$CH_2$ CO— (where X=Br, Cl or I). These sulfhydryl groups will also react with imidazolyl, thioether, phenol and amino groups. N-maleimide derivatives are also selective towards sulfhydryl groups, but can additionally be useful in coupling to amino groups under certain conditions. Examples of reactive functional groups capable of reaction with amino groups include alkylating and acylating agents.

Representative alkylating groups include N-maleimide derivatives; aryl halides, such as reactive nitrohaloaromatic compounds; aldehydes and ketones capable of Schiff's base formation with amino groups; epoxide derivatives such as epichlorohydrin and bisoxiranes, which can react with amino, sulfhydryl or phenolic hydroxyl groups; chlorine-containing derivatives of s-triazines, which are very reactive towards nucleophiles such as amino, sufhydryl and hydroxy groups; $\alpha$-haloalkyl ethers.

Representative amino-reactive acylating agents include isocyanates and isothiocyanates; sulfonyl chlorides, acid halides; active esters, such as nitrophenylesters or N-hydroxysuccinimidyl esters; acid anhydrides; acylazides; and imidoesters, which form stable amidines on reaction with amino groups.

Coupling between the targeting vector and the surfactant can also be effected with certain enzymes. For example, transglutaminase, peroxidase and xanthine oxidase can serve as enzyme linkers.

Spacers

Spacer elements separating the reactive groups of a bifunctional or polyfunctional linker can be aliphatic chains of 2 to 10 bonds. There can be other macromolecular structures, such as poly(ethylene glycols) (PEG's). Appropriate molecular weights for PEG spacers used in accordance with the invention will be between 120 and 20,000.

It can be desirable that the targeting ability and stability of the product change over the residence time of the agent in the body. Thus, it can be desirable for the spacer to have labile linkages. For example, it may contain arms that are biodegradable, chemically sensitive or enzymatically cleavable. Representative cleavable spacer elements include, but are not limited to, vicinal glycol, azo, sulfone, ester, thioester and disulfide groups.

As an example of the practice of this aspect of the invention with surfactants made from linkers having cleavable spacers, the cleavable spacer can contain arms of PEG, which serve to inhibit clearance of the agent by the RES. As the arms separate from the spacer, uptake of the particle by the RES increases, ultimately leading to complete removal of the contrast agent from the body.

Alternatively, a linker with a cleavable spacer can connect the surfactant with a targeting vector. Cleavage of the linker will allow the metal particle to separate from the targeting vector, and consequently the receptor sites, following imaging.

Other representative spacer elements include, but are not limited to, polysaccharides, such as polygalacturonic acid; glycosaminoglycans; heparinoids; cellulose and marine polysaccharides, such as alginates, chitosans and carrageenans; storage-type polysaccharides, such as starch, glycogen, dextran and aminodextrans; polyamino acids and methyl and ethyl esters thereof, such as homo-and copolymers of lysine, glutamic acid and aspartic acid; and polypeptides, oligonucleotides and oligosaccharides. Each of these may or may not contain enzyme cleavage sites.

Other potentially useful polymeric spacer materials include copolymers of methyl methacrylate with methacrylic acid; block copolymers of polymethacrylates with biodegradable polyesters; cyanoacrylates, i.e. polymers of esters of 2-cyanoacrylic acid; polyvinyl; copolymers of vinyl methyl ether with maleic anhydride; polyvinylpyrrolidones; polymers and copolymers of short-chain aliphatic hydroxy acids such as glycolic, lactic, butyric, valeric and caproic acids; polyesters consisting of alternating units of ethylene glycol and terephthalic acid; block copolymers comprising biodegradable segments of aliphatic hydroxy acid polymers; polyurethanes; poly(1,4-dioxan-2-ones; polyanhydrides, such as copolymers of sebacic acid (octanedioic acid) with bis(4-carboxy-phenoxy)propane; biodegradable polymers containing ortho-ester groups; polyphosphazenes, which are inorganic polymers consisting of alternate phosphorus and nitrogen atoms.

Spacers of many other types are well known to those practiced in the art, as taught in the patents in the reference list, which are hereby incorporated in their entirety by reference.

Modifiers

The invention encompasses the attachment to the surfactant, through one or more linking groups and optional spacer, of various types of modifiers to control the biological and chemical properties of the metal particle-surfactant complex.

Examples of the many types of structures that are possible for the modifiers include, but are not limited to, the following:

(i) Synthetic polymers, especially hydrophilic polymers such as PEG derivatives, that prolong the residence time of the agents in the blood after intravascular injection.

(ii) Natural or synthetic peptides having a high degree of resistance to degradation by vascularly circulating esterases, amidases, or peptidases. A useful method of stabilization of peptide moieties incorporates the use of cyclization techniques. As an example, the end-to-end cyclization whereby the carboxy terminus is covalently linked to the amine terminus via an amide bond may be useful to inhibit peptide degradation and increase circulating half-life. Additionally, a side chain-to-side chain cyclization or end-to-side chain cyclization is also useful in inducing stability. In addition, the substitution of an L-amino acid for a D-amino acid in a strategic region of the peptide may offer resistance to biological degradation. In an especially useful embodiment of the invention, these resistive modifiers will be attached to the surfactant through cleavable spacers.

(iii) Sugars, including monosaccharides, polysaccharides and other carbohydrates. These will further protect the metal particles of the invention to uptake by the RES. In an especially useful embodiment of the invention, these sugars will be attached to the surfactant through cleavable spacers.

(iv) Therapeutic materials, such as drugs and pro-drugs. These may include activators for photodynamic therapy as well as agents for chemotherapy.

Targeting Vectors

A particularly useful class of optional modifiers for attachment to the surfactants of the present invention comprises targeting vectors, which are substances capable of preferential adhesion to chemical or biological groups specifically associated with certain types of tissue, disease lesions or other substances in the body. Targeting vectors may additionally modify the chemical and physical properties of the contrast agents.

Collectively the adhesion sites are known as targeting receptors. Preferably, the targeting receptors are certain types of chemical or biological groups that are overexpressed by the cells of certain tissues of interest, such as cancerous tumors or other disease sites or are exclusively associated with the cells of certain tissues of interest. The targeting receptors may normally be located on the surfaces of the target cells, in the interiors of target cells, or in the extracellular fluid surrounding the target cells. The receptor sites may normally be released into the extracellular fluid or may be released as a result of disease, such as inflammation or tumor growth, or trauma. A targeting ligand directed toward thrombotic material in plaque may be used to differentiate between active and inactive regions of atherosclerotic plaque.

Preferred targeting vectors may be selected from the following species or biological or chemical substances:

(i) Antibodies and antibody fragments. These have the advantageous property of very high affinity for specific receptor sites. Both conventional and genetically engineered antibodies may be employed, the latter permitting engineering of antibodies to maximize such properties as affinity and specificity. The use of human antibodies may be preferred to avoid possible immune reactions against the vector molecule. Antibodies may be employed, for example, to target endoglin, which is an endothelial cell proliferation marker. A targeting ligand that may be used to target endoglin is the antibody TEC-11 (Thorpe et al., 1995.). Further, antibodies directed to cadherins, such as, for example, the monoclonal antibody Ec6C10, may be used to recognize cadherins expressed locally by specific endothelial cells.

(ii) Proteins and glycoproteins other than antibodies and antibody fragments. An example of a protein that may be useful as a targeting vector is Protein A, which is produced by most strains of *Staphylococcus aureus*, is commercially available from Sigma Chemical Co. (St. Louis, Mo.) and may be used for binding a variety of IgG antibodies. Other useful proteins include cytokines, integrins, growth factors, cadherins, immunoglobulins, peptide hormones, lectins, selectins and pieces thereof. Growth factors, including, for example, basic fibroblast growth factor (bFGF), may be useful for targeting endothelial cells the vascular system produced in many tumors through the process of angiogenesis. Lectins may be useful in targeting endothelial-leukocyte adhesion molecules (ELAM's), which are antigens that are expressed by endothelial cells under conditions of stress.

(iii) Oligopeptides, polypeptides, amino acids and other protein components or protein fragments.

(iv) The cadherin family of cell adhesion molecules may also be used as targeting vectors for endothelial cells. These include the E-, N-, and P-cadherins, cadherin-4, cadherin-5, cadherin-6, cadherin-7, cadherin-8, cadherin-9, cadherin-10.

(v) Sugars, including monosaccharides, polysaccharides and other carbohydrates. Particle surfaces, either modified with sugars through direct coating or through attachment of the sugar to a surfactant indirectly with the particle surface, will be recognized in vivo by oligosaccharide receptors, such as the asiologlycoprotein receptor. In some cases, sugars may be used to target ELAM's.

(vi) Vitamins, cofactors for vitamins and modified forms thereof. An example is folic acid and derivatives of folic acid.

(vii) Steroids, steroid analogs and modified forms thereof.

(viii) Cholesterol may be used to target endothelial cells, especially in atherosclerotic plaque.

(ix) Genetic material, including nucleosides, nucleotides, oligonucleotides, polynucleotides and modified forms of nucleosides, nucleotides, oligonucleotides, polynucleotides and other substances that bind to DNA or RNA, either through Watson-Crick pairing or through some other type of interaction. DNA is usually only present in extracellular space because of cell damage, so that such oligonucleotides may be useful for targeting necrotic tissue, which is found in some malignant tumors and other disease sites. Oligonucleotides may also be designed to bind specifically to transcription factors, which are very often highly overexpressed or activated in tumor cells or in activated immune or endothelial cells. Combinatorial libraries may be used to select oligonucleotides that bind specifically to possible target molecules.

(x) Synthetic compounds that combine a natural amino acid sequence with sequences not normally found in nature. Besides natural ligands for biological receptors, synthetic ligands that mimic biological receptors are also suitable.

(xi) A completely synthetic chemical structure, that is a chemical construct not normally found in nature, with a special affinity for one or more naturally occurring receptor sites.

Those skilled in the art will recognize that many other types of targeting vectors are also possible. Examples of other types of targeting vectors for particulate contrast agents include, but are not limited to, those described in U.S. Pat. Nos. 6,331,289, 6,264,917, 6,403,056, which are hereby included in their entirety by reference.

An alternative way to classify targeting vectors is in terms of the receptor sites to which they bind. It should be obvious that there is a complementarity between targeting vectors and receptor sites. Thus, the roles of targeting vectors and receptor sites can be exchanged in certain situations. Chemical species that act as receptor sites, when identified, can be turned into targeting vectors.

The receptor sites for the targeting vectors of this invention may belong, but are not limited to, the following groups:

(i) Proteins or peptides to which glucosaminoglycan side chains bind.

(ii) Sites on atherosclerotic plaque.

(iii) Sites on myocardial cells. Examples of targeting vectors for myocardial cells include, but are not limited to, anti-cardiomyosin antibody, which may comprise polyclonal antibody, and Fab'2 fragments. Additional targeting ligands include dipyridamole; digitalis; nifedipine; apolipoprotein, ryanodine; endothelin, dihydropyridine; adenosine; mineralocorticoid; antibodies to the human alpha 1A-adrenergic receptor; bioactive agents, such as drugs, including the alpha 1-antagonist prazosin; antibodies to the anti-beta-receptor; drugs that bind to the anti-beta-receptor, and endothelin-1.

(iv) Interleukin-1 or interleukin-2.

(v) Lymphocytes such as T-cells or B-cells, with T-cells being the preferred target. An anti CD-4 antibody can be used for selecting the class of T-cells harboring CD4 receptors; an anti CD-8 antibody can be used for selecting the class of T-cells harboring CD-8 receptors; an anti CD-34 antibody can be used for selecting the class of T-cells harboring CD-34 receptors; etc.

(vi) Sites specific to the network of new blood vessels typically formed by of angiogenesis in many cancerous tumors as described in U.S. Pat. No. 6,139,819, which is incorporated in its entirety by reference. Angiogenesis is the process of formation of new blood vessels branching from existing vessels in a malignant tumor. It is essential to the growth of most cancerous tumors, and its detection is an important means of discovering developing tumors.

(vii) Endothelial-leukocyte adhesion molecules (ELAM's) are antigens that are expressed by endothelial cells under conditions of stress. The endothelial cells facilitate the migration of the leukocytes across the endothelium lining of the vasculature into the surrounding tissues. A wide variety of different targeting vectors can be selected to bind to the cytoplasmic domains of the ELAM molecules.

In some situations, it will be possible to practice this invention without knowing the chemical identity of the receptor site. In this case, it may nevertheless be possible to select a targeting vector for the tissue or other body structure of interest by functional searching for molecular structures adhering to the target tissue or other body component. Selection from a combinatorial library will be especially effective for identification of an appropriate targeting vector.

The invention encompasses the use of ambiphilic targeting vectors that coat the surface of the metal particles without the need for covalent binding with a surfactant. More commonly, the targeting vector will be covalently attached to a surfactant that interacts with the surface of the particle through van der Waals forces or other physical interactions.

Complexation of Gold Rods with Antibodies

The following is a generalized procedure for complexation of gold rods with antibodies and follows the outline of Beesley, 1989. A similar procedure can be used to form complexes of gold rods and other proteins, such as enzymes and lectins.

The solution of the antibody (1 mg/ml) is dialyzed with the pH of the solution adjusted to the isoelectric point of the antibody. The buffer solution of the antibody is then centrifuged at 100,000 g for 1 h at 4° C. to sediment any antibody aggregates.

The pH of a colloidal suspension of naked gold nanorods (no polymeric stabilizer) is brought to the isoelectric point of the antibody with $K_2CO_3$, and 10 aliquots of 0.5 ml are removed. To each of these is added an aliquot of the antibody solution diluted to a different concentration. After the solutions of the antibody and the gold particles have been allowed to sit for 1 min, 0.1 ml of 10% NaCl solution is added to each with agitation. The solution with the least amount of protein that does not change color from red to blue is selected. The antibody concentration of this solution is the least sufficient for particle stabilization.

The appropriate protein concentration determined by the procedure of the previous step, plus 10%, is added to a working aliquot of the gold particles. After 5 min, a filtered solution of 1% w/v PEG in distilled water is added in the amount of 1% of the complete volume of the colloidal gold/antibody suspension. The mixture is stirred for an additional 5 min. The complex is centrifuged for 2 hr at 18,000 rpm. All but about 1 ml of the supernatant is aspirated and discarded. A soft pellet, which contains the gold-antibody complex, is gently away from a solid pellet stuck to the tube surface. The soft pellet is then re-suspended in the remaining 1 ml of supernatant to give a stock solution, which is microcentrifuged at 18,000 rpm for 30 min just prior to use.

Antibody complexes of gold nanorods can be targeted to cancerous tumors. A selective nanoparticles accumulation in cancer cells or tumors can be demonstrated using transmission electron microscopy and scanning electron microscopy. A direct linking protocol may be employed for conjugation of metallic nanospheres with humanized IgG-antibody. An optimal concentration of protein attached to nanoparticles is about 60 nmole/litre.

Those skilled in the art can recognize that a targeting vector against cancer receptor may be used not only for detection purposes, but also for therapeutic purposes. This conclusion comes with understanding that targeting vectors (such as monoclonal antibody, mab) attached to protein receptors on the surface of cancer cells may disable vital functions of those receptors and thereby kill those cancer cells. An example of such therapeutic action is a mab commercially known as Herceptin, raised against receptors associated with HER2/neu gene overexpressed in breast cancer cells and other types of cancer. Herceptin has been successfully used for treatment of metastatic breast cancer [J. S. Ross, G. S. Gray: Targeted therapy for cancer: the HER-2/neu and Herceptin story, *Clin Leadersh Manag Rev.* 2003; 17(6): 333-340]. We teach that one possibility to produce an optoacoustic contrast agent based on elongated at least partially metallic nanoparticles is through attachment of antibodies to the designed nanoparticles. In association with previously disclosed therapeutic effect of targeting vectors, we anticipate that the optoacoustic contrast agent disclosed in this application also can be used as an anticancer therapeutic agent.

Particle Aggregates

The invention further encompasses the use of contrast agents for optoacoustic imaging comprising aggregates of spherical or non-spherical metal particles.

The invention further encompasses the use of aggregates of metal particles of any shape for which the shape, composition, and dimensions of the aggregates and the shape, composition, and dimensions of the particles which they comprise are chosen for maximal absorption of the radiation used for optoacoustic imaging. Preferably, the choice of the shape, composition, and dimensions of the aggregates and the shape, composition, and dimensions of the particles which they comprise particles will place the absorption maximum of the aggregates near the irradiation wavelength. More preferably, the choice of the shape, composition, and dimensions of the aggregates and the shape, composition, and dimensions of the particles which they comprise particles will place the absorption maximum of the aggregates near the irradiation wavelength and will maximize the absorption for light absorption at that wavelength. Preferred aggregates are two- and three-dimensional structures comprised of even numbers of elongated nanoparticles (two- and three-dimensional stars, pyramids, etc.).

Methods for organizing metal nanoparticles into stabilized aggregates are known. Storhof et al. (2000) and Dujardin et al. (2001) teach that covering the surface of different gold particles with complementary strands of DNA favors the self-assembly of the particles into ordered aggregates. Aggregate formation results from the favorable interaction between the complementary strands of DNA. The invention comprises the use of contrast agents for optoacoustic imaging comprising aggregates of particles coated with complementary strands of artificial or natural DNA, RNA or analogs of RNA or DNA.

In another embodiment of the invention, the contrast agents comprise aggregates of metal particles. Such aggregates will exhibit a collective plasmon resonance that will enhance the intensity of the optoacoustic signal over that expected for single particles. For example, a cubic stack of 16 nanorods (4 layers with 4 nanorods in each layer) will absorb more optical radiation than 16 separate nanorods. The presence of a collective plasmon resonance for a collection of nanoparticles is evidenced experimentally by a non-linear increase in the intensity of the optoacoustic signal as the particle concentration increases and aggregates are formed.

A useful means of promoting controlled particle aggregation is to coat different particles with complementary components of genetic material. "Genetic material" refers to nucleotides, oligo- and polynucleotides, including deoxyribonucleic acid (DNA) and ribonucleic acid (RNA) and the components of nucleotides, oligo- and polynucleotides. The genetic material may be made by synthetic chemical methodology known to one of ordinary skill in the art, or by the use of recombinant technology, or by a combination thereof. The DNA and RNA may optionally comprise unnatural nucleotides and may be single or double stranded. "Genetic material" also refers to sense and anti-sense DNA and RNA, which are nucleotide sequences that are complementary to specific sequences of nucleotides in DNA and/or RNA. "Genetic material" also refers to synthetic analogs of naturally occurring substances, for example, analogs made with sugars other than ribose or deoxyribose.

Liposomes

In still another embodiment of the invention, the metal particles may be encapsulated in liposomes are other types of lipid vesicles, either as individual particles or aggregates of particles. As known in the art, liposomes are vesicles made from phospholipids in which a lipid phase encapsulates an aqueous phase. Examples of phospholipids are dipalmitoylphosphatidylglycerol (DPPG) and dipalmitoylphosphatidylcholine (DPPC). The lipid wall can be strengthened, when needed to prevent leakage, by cholesterol. The liposomes preferably have a size of about 0.02 to 2.0 microns and preferably have a size less than 1.0 micron.

The liposomes are prepared by standard procedures as known in the art. For example, the metal particle can be dispersed in the phospholipid before it is mixed with the aqueous phase. The organic phase is then removed from the mixture and the resulting lipid vesicles are recovered.

Formulations

The present invention contemplates a wide variety of formulations of the contrast agents to be used in the practice of the invention. In general, the particulate portion of the contrast agent will be dispersed in a sterile carrier liquid, which may be water, a water solution such as saline solution, an organic liquid, or an oil, including oils of animal, mineral or synthetic origin. The carrier may also be a mixture of several components. Examples of suitable organic liquids include, but are not limited to, methyl, ethyl, or isopropyl alcohol, acetone, glycerol, and dimethylsulfoxide. Examples of suitable oils include, but are not limited to, canola oil, soybean oil, mineral oil, and sesame oil. Water or saline solution are preferred carriers when the mode of administration is intravenous or intra-arterial injection.

The formulations used for practice of the invention can include a variety of excipients. The formulation may further comprise, for example, one or more chemical stabilizers, neutral lipids, charged lipids, gases, gaseous precursors, liquids, oils, diagnostic agents, and/or bioactive agents.

The present invention further anticipates the use of a contrast agent for optoacoustic imaging in conjunction with therapy. Therefore, the composition may contain adsorbed drugs or pro-drugs.

Appropriate topical formulations will have applications in imaging and/or therapy of the skin, subcutis and adjacent regions and organs, for example in targeting the peripheral circulation of body extremities such as legs.

Formulations of the contrast agent for administration orally or by injection may be prepared as solutions in or mixtures with water and/or one or more water-miscible and physiologically acceptable organic solvents such as ethanol, glycerol or polyethylene glycol.

Method of Administration

The invention will be especially useful with respect to medical imaging of a human or non-human body. However, various other uses for the invention are also anticipated. For example, the method will be useful for the sensitive detection of environmental pathogens, such as harmful bacteria and spores of harmful biological agents. When a suspected pathogen is examined, it will generally be sufficient that the test sample simply be bathed in the formulation containing the contrast agent.

For imaging of a human or a non-human body, many modes of application are possible, depending on the imaging requirements. Administration of the contrast agent may be systemic or local. The modes of administration include, but are not limited to the possibilities described in the following paragraphs.

Aqueous liquid suspensions may be placed in the gastrointestinal tract by oral ingestion or may be inserted by a syringe. The agent may be injected with a hypodermic syringe. Modes of injection include, but are not limited to intramuscular, intra-arterial, intravenous, intradermal, intraperitoneal, and subcutaneous. For intra-arterial or intravenous injection, the agent may be injected into the vascular system as a whole or into the vessels of a specific organ. For imaging of cancerous tumors, it will sometimes be preferable that the agent be directly injected into the tumor. When the compositions of the invention are injected subcutaneously, the metal particles may be taken up by the lymph system, thereby facilitating imaging of lymph nodes. Injection may involve some mechanism of controlled release. For example, a pump that administers the agent at a controlled rate may be used.

Local administration of the contrast agent may be accomplished by topical application, by means of a catheter, with a suppository, or by means of an implant. Other means of local application will be apparent to those skilled in the art.

In one embodiment of the invention, the contrast agents are administered in conjunction with the use of hyperthermia, that is, the artificial elevation of the local temperature of an organ or another body part. Kong, et al. (2000 and 2001) teach that hyperthermia accelerates the passage of nanoparticles through the capillaries of the vascular system of growing tumors. Hyperthermia will also enhance the uptake of the contrast agent of other types of diseased tissue, sites of inflammation caused by infection or trauma.

Any of many different means of elevating the temperature are possible. These include, but are not limited to, the application of warm baths, the use of focused ultrasound, microwave irradiation (with or without the prior injection of a microwave-absorbing substance), heating of the blood passing through the organ, and chemical heating. Any or all of these heating procedures can be actively applied while the contrast agent is applied, or the heating can take place up to 24 hours prior to the administration of the agent.

Imaging

Oraevsky et al. teach the acquisition of optoacoustic images with contrast agents in U.S. Pat. No. 5,840,023. In their method, a short pulse of irradiation is followed by detection of the induced pressure wave, which is then used for generation of an image.

In the practice of the present invention, the pulses of electromagnetic radiation will preferably have a duration of 10 ns to 1000 ns. When the tissue to be imaged is simulated by a solid slab tissue, the radiation fluence on the surface of the slab will be about 10 mJ/cm$^2$. For other configurations of the test sample, or for living human or non-human bodies the surface fluence will vary, but will always be in the range 1 to 100 mJ/cm$^2$, which generally is considered safe.

The practice of the present invention is not limited to the methods of U.S. Pat. No. 5,840,023 and encompasses the acquisition of an optoacoustic image with the aid of contrast agents comprising non-spherical at least partially metallic nanoparticulates, which may comprise a single metal or may be composites of different metals or may be filled metal shells, tuned to the wavelength of the irradiation, which may be anywhere in the electromagnetic spectrum from about 3 nm to about 300 mm. However, wavelengths in the visible or infrared range from about 450 nm to about 1500 nm are preferred. More preferred is irradiation in the near-infrared wavelength range from 650 to 1200 nm. The irradiation can be generated with a laser, but the invention encompasses the use of any radiation source, regardless of whether it can be called a laser or not.

The invention also anticipates optoacoustic imaging with irradiation at two or more wavelengths, either simultaneously or sequentially, with the aid of contrast agents comprising non-spherical at least partially metallic nanoparticulates tuned to the wavelength of the irradiation, which may be anywhere in the electromagnetic spectrum.

The imaging can occur during administration of the contrast agent, immediately after administration, or at some later time to allow for accumulation of the agent in the target organs or diseased lesion.

EXAMPLE I

Optical Absorption Spectra of Metal Nanoparticles

To calculate the intensity and resonance absorption of an ellipsoid metal nanoparticles (NP) with radii, a and b and length, c, it is necessary to know the amplitude of an electromagnetic field inside the NP. When the wavelength is significantly longer than the linear dimensions of NP, the E-field components, $E_k$, inside the NP can be expressed in terms of the external field, $E_{O_k}$, incident upon metal NP as taught by Papavassilliou-1980, who provided details to a classical electromagnetic theory described by Stratton-1941:

$$E_{m_k} = \frac{\varepsilon_0}{(\varepsilon_m - \varepsilon_0)P_k + \varepsilon_0} E_{0_k} \quad (1)$$

where $\varepsilon_m = \varepsilon'_m + i\varepsilon''_m$ is the dielectric constant of the metal, from which NP is fabricated, $\varepsilon_0$ is the dielectric constant of the surrounding medium (usually can be taken with properties of water). It is assumed that the axes x, y, z are directed along the NP axes. The quantity $P_k$ {k=x,y,z} is called the depolarization factor along axes x, y, z is determined by the integral:

$$P_k = \frac{1}{2}\int_0^\infty \frac{abc}{(s+d_k^2)\sqrt{(s+a^2)(s+b^2)(s+c^2)}} ds \quad (2)$$

where $d_x \equiv a$, $d_y = b$, $d_z = c$ are the ellipsoid axes as shown in FIG. 1.

The expression (1) is strictly valid in the range of limited nanoparticles dimensions:

$$c < d_{max}(\lambda) \equiv \frac{\lambda}{2\pi\sqrt{|\varepsilon(\lambda)|}} \quad (3)$$

where $\lambda$ is the wavelength of optical (electromagnetic) irradiation, c is the longest axis of the nanoellipsoid. We experimentally determined that the factor of 3 satisfies the condition requiring maximum size of NP to be much smaller than the electromagnetic wavelength.

For a nanosphere (a=b=c) $P_k=2/3$ and one can get the following simplified equation:

$$E_{m_k} = \frac{3\varepsilon_0}{\varepsilon_m + 2\varepsilon_0} E_{0_k} \quad (4)$$

In the case when $\varepsilon''_m \ll \varepsilon'_m$ (which is true for noble metals such as silver and gold), we have a classical plasmon resonance where electromagnetic field dramatically increases inside the nanoparticles under the resonance condition of:

$$\varepsilon'_m + 2\varepsilon_0 = 0 \quad (5)$$

The calculation using Eq. (5) shows that the plasmon resonance of gold nanospheres lies at $\lambda$=520-nm and for silver nanospheres $\lambda$=390-nm.

For ellipsoids of revolution (a=b) and its length, c, is directed parallel to the z-axis.

Therefore, the depolarization factor along the z-axis can be expressed as:

$$P_\|(\zeta) = \frac{1}{2}\int_0^\infty \frac{a^2 c}{(s+c^2)^{3/2}(s+a^2)} ds \quad (6)$$

$$= \frac{1}{2}\int_0^\infty \frac{\zeta}{(s'+\zeta^2)^{3/2}(s'+1)} ds',$$

$$\zeta = \frac{c}{a} = \frac{c}{b} > 1$$

where $\zeta$ is the aspect ratio of the ellipsoid, i.e. ratio of long axis to the short axis, s is the running spatial coordinate in x, y, z space (parameter that changes from 0 to $\infty$). It was convenient in Eq. (6) to replace running parameter, s with s'=s/$a^2$.

For the electrical field perpendicular to the z-axis (long axis of the ellipsoid c), we have:

$$P_\perp(\zeta) = \frac{1}{2}\int_0^\infty \frac{a^2 c}{(s+a^2)^2(s+c^2)^{1/2}} ds \quad (7)$$

$$= \frac{1}{2}\int_0^\infty \frac{\zeta}{(s'+1)^2(s+\zeta^2)^{1/2}} ds'$$

In the approximation when the characteristic linear dimension of nanoellipsoid is small compared with the wavelength of irradiation, one can calculate the power density, W, absorbed by the unit volume of the metal nanoellipsoid:

$$W(\lambda, \zeta) = \frac{\varepsilon''_m}{2\lambda} \sum_k \frac{\varepsilon_0^2}{[P_k(\zeta)\varepsilon'_m(\lambda) + (1-P_k(\zeta))\varepsilon_0]^2 + [P_k(\zeta)\varepsilon''_m(\lambda)]^2} |E_{0_k}|^2 \quad (8)$$

Expression (8) demonstrates that the effect of the ellipsoid shape and its orientation with respect to the electric field is determined by the coefficients $P_k$, which in turn depends according to (6,7) only on one parameter, aspect ratio, $\zeta$, related to another parameters, e and q, convenient for use in our further calculations:

$$e = \sqrt{1 - \left(\frac{c}{a}\right)^2} = \sqrt{1 - \left(\frac{c}{b}\right)^2} = \sqrt{1 - q^2} = \sqrt{1 - \frac{1}{\zeta^2}} \quad (9)$$

The Eq.(8) permits theoretical calculation of the absorption spectra for nanoparticles of various shapes and diameters (spheres and ellipsoids) as presented in FIG. 1. FIG. 1 depicts absorption spectra of gold nanoparticles with equal volume but different shapes, showing significantly increased absorbance of prolate nanoparticles relative to spherical nanoparticles and absorbance of shells relative to full-body nanoparticles.

Optical radiation is often not polarized, especially when propagating through biological tissues. Therefore, when calculating absorbed energy (Eq. 8) one needs to take coefficients $P_k$ integrated over the range of all angles between nanoparticles axis of revolution and the electrical field. The resulting equation shows that the total absorption coefficient will be decreased 3 times relative to the situation of electrical field parallel to the nanoparticles axis (Eq. 6).

The optical absorption spectrum of a collection of randomly oriented gold nanorods with aspect ratio $\zeta$ can be modeled by using an extension of Mie theory for prolate particles (Papavassilliou, 1980). According to (Gans, 1915) the molar extinction coefficient $\sigma_{mole}$ for N particles of volume V is given within the dipole approximation by the following equation:

$$\sigma_{mole} = \frac{2\pi N V \varepsilon_0^{3/2}}{3\lambda} \sum_j \frac{\left(\frac{1}{P_k^2}\right)\varepsilon''_m}{\left(\varepsilon'_m + \frac{1-P_k}{P_k}\varepsilon_0\right)^2 + \varepsilon''^2_m} \quad (10)$$

-continued $$P_x = \frac{1-e^2}{e^2}\left[\frac{1}{2e}\ln\left(\frac{1+e}{1-e}\right)-1\right] \quad (11)$$

$$P_x = P_y = P_\perp = \frac{1-P_z}{2} = \frac{1-P_\parallel}{2} \quad (12)$$

Figure 2:
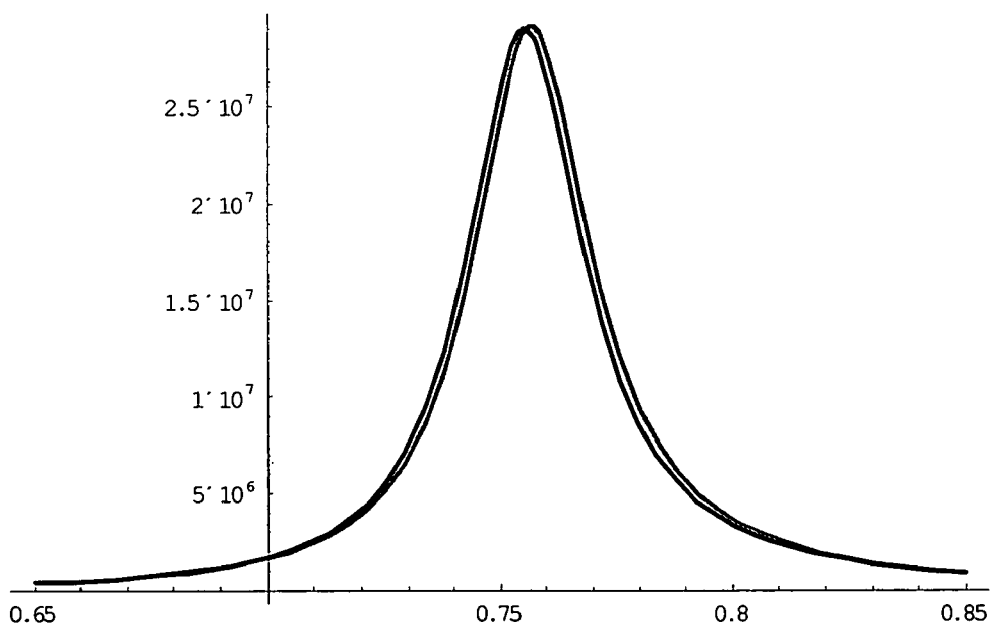

As anticipated, calculation of the 2 systems of Equations (6,7,8) and (10,11,12) yields very similar results demonstrated by two very close curves in FIG. 2.

In order to employ Eq. 8 (deduced for nanoellipsoids) for calculation of nanorod absorbance, one needs to replace coefficient 2 (for ellipsoids) in the nominator of Eq. 6 with the coefficient 3 (for nanorods). The position of maximum on the absorption spectrum of metal nanorods embedded in a medium with dielectric permeability of 1 can be described by the following numerically calculated approximate solution for the Mie-Gans equation (Gans, 1915; Papavassiliou, 1980; Link, 1999), which is practically useful due to its simplicity:

$$\lambda_{max} = (33.34\zeta - 46.31)\epsilon_0 + 472.31 \quad (13)$$

One and the same aspect ratio in nanorods and nanoellipsoids yields a slightly different position of the absorption maximum. For example, maximum of absorption will be located at the wavelength of 760-nm for nanorods with aspect ratio 3.6 and for nanoellipsoids with aspect ratio of 4. The difference also occurs if one takes table data for nanoparticle material from different sources.

We also teach that coating of metal nanoparticles with dielectric shells (such as protein) changes position and strength of absorption maximum of the nanoparticles, especially in elongated nanoparticles, which can be utilized in optoacoustic detection and imaging.

Figure 3:
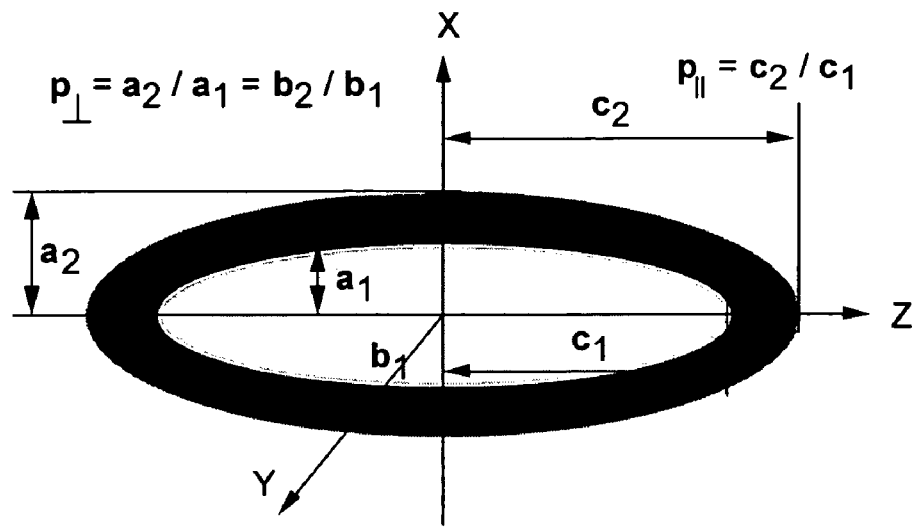
FIG. 3. Geometry and definitions of a prolate spheroidal nanoparticle.
Figure 4:
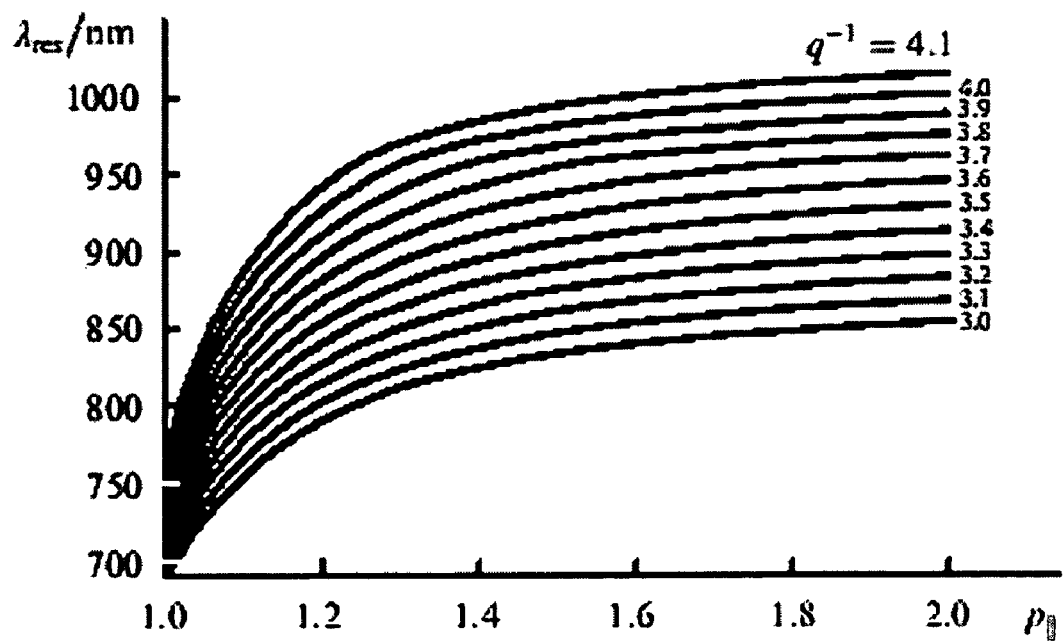
FIG. 4. Dependences of $\lambda_{res}$ on $p_\parallel$ for a gold nanoellipsoid of volume $10^4$ $nm^3$ with a protein shell, placed in water and oriented parallel to the incident electrical field for different q.
Figure 5:
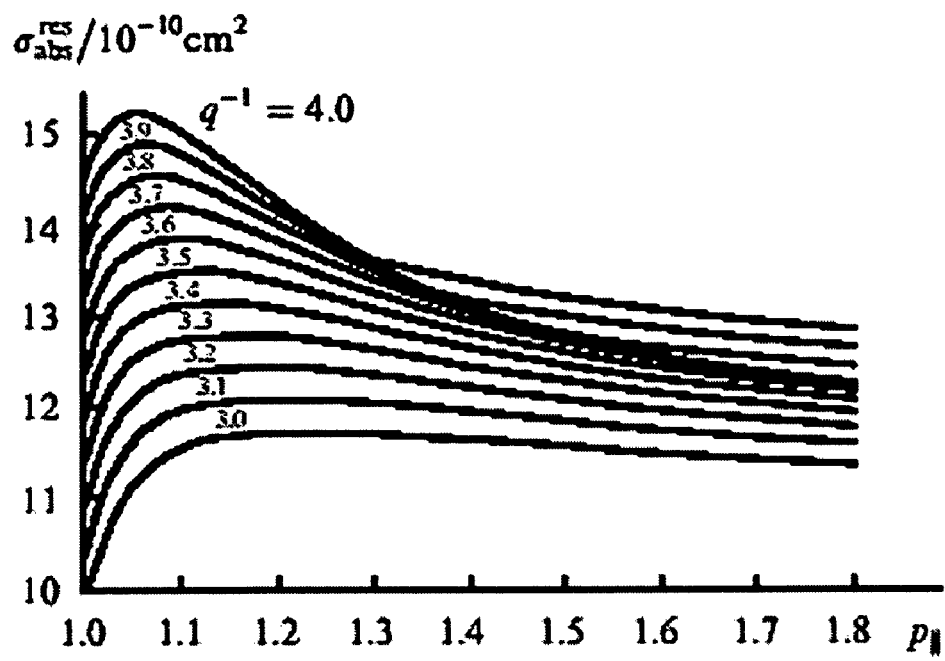
FIG. 5. Dependences of on $p_\parallel$ for a gold nanoellipsoid with a protein shell in water oriented parallel to the incident electrical field for different q.

Referring now to FIG. 3, let us consider optical absorption by a metal ellipsoid of revolution surrounded by a dielectric shell. Such a structure can be formed, for example, when a metal nanoparticle penetrates into a biological tissue of a microorganism or a metal particle coated with protein or other biopolymers. We discuss here the properties of absorption of light by such a nanoparticle by the example of a gold ellipsoid surrounded by a dielectric shell with the dielectric constant $\epsilon_d \approx 4$ and placed in water. We assume that the nanoellipsoid has a parallel orientation to the electrical field in the laser beam because in this case the properties of a nanoparticle manifest their utility for optoacoustic imaging in the near-infrared spectral range.

The absorption cross-section of a nanoparticle with the parallel orientation (the complex dielectric constant of the metal core is $\epsilon_m$ and the dielectric constant of the dielectric shell is $\epsilon_d$) in surrounding medium with the dielectric constant $\epsilon_0$ in the form of $$\sigma_{abs} = V_m p_\parallel^2 \frac{e^4}{q^4}\epsilon_0^2\epsilon_d^2 \text{Im}\epsilon_m \frac{2\pi}{\lambda}|\gamma^{(\parallel)}|^2 \quad (14)$$

where $V_m$ is the volume of the metal nanoellipsoid, $$\lambda = \frac{2\pi c}{\omega}$$

is the wavelength of incident electromagnetic wave, $p_\parallel$ and $p_\perp$ are the ratios of protein shell diameter and nanoparticle diameter in directions parallel and perpendicular to the electric field (see FIG. 3), $\gamma^{(||)}$ is the coefficient dependent on geometry and dielectric properties of nanoparticles and surrounding medium:

$$\gamma^{(||)} = \frac{e^2}{p_\perp^2 q^2}\left\{\begin{matrix}(\varepsilon_s-\varepsilon_m)\left[\varepsilon_0\frac{e^2}{p_\perp^2q^2}+\frac{e^2}{2q^2}B^{(||)}(\varepsilon_s-\varepsilon_0)\right]\times \\ \frac{e^2}{2q^2}(p_{||}A^{||}-B^{||})-\varepsilon_s\frac{e^2}{2q^2}B^{(||)} \\ \left[(\varepsilon_s-\varepsilon_0)p_{||}\frac{e^2}{q^2}-(\varepsilon_s-\varepsilon_m)\frac{e^2}{p_\perp^2q^2}\right] \\ -\varepsilon_0\varepsilon_s\frac{e^2}{p_\perp^2q^2}p_{||}\frac{e^2}{q^2}\end{matrix}\right\}^{-1} \tag{15}$$

$$\text{taking } A^{(||)} = -\frac{2q^2}{e^2}\left[1-\frac{1}{2e}\ln\left(\frac{1+e}{1-e}\right)\right]; \tag{16}$$

$$B^{(||)} = -\frac{2q^2}{e^2}\left[1-\frac{p_{||}}{2e}\ln\left(\frac{p_{||}+e}{p_{||}-e}\right)\right]$$

The expression (14) was obtained by integrating expression for the absolute value of the electrical field (derived in J. A. Stratton, "Electromagnetic Theory", NY, McGraw-Hill, 1941) directed parallel to the axis of a nanoellipsoid over the volume $V_{mne}$. The expression for the absorption cross section in the case of perpendicular orientation can be obtained a similar way by integrating the absolute value of the electrical field directed perpendicular to the axis of nanoellipsoid over the volume $V_m$.

Our calculation shows that the absorption cross section, $\sigma_{abs}^{res}$, has a resonance shape as function of the wavelength. The resonance wavelength corresponding to the maximum of the absorption cross section depends on the dielectric shell thickness (FIG. 4). Referring to FIG. 4, as the shell thickness increases (for the given volume of the nanoellipsoid and the given aspect ratio, q), the resonance wavelength, $\lambda_{res}$, also increases, tending to the limiting value corresponding to the case when the ellipsoid is placed in an infinitely extended medium. Note also that $\lambda_{res}$ also increases with increasing aspect ratio of the nanoparticle, $q^{-1}$.

The dependence of the resonance maximum of the absorption cross-section, Equation (14), on the shell thickness is shown in FIG. 5. One can see that, for the specified aspect ratio, $q^{-1}$, there exists the optimal thickness of the shell providing the maximum of the absorption cross-section. However, in the region of large values of $p_{||}$, a nonmonotonic variation in the absorption cross section can be expected for the given wavelength. This is explained by the appearance of resonances when the shell size becomes comparable with the wavelength in the dielectric.

The effects depicted in FIG. 4 and FIG. 5 have significant value for potential applications of nanoparticles as contrast agents. A nanoparticles designed to absorb optical radiation only when coated with a dielectric nanoshell of protein will lose its absorption at a given wavelength in case the shell is absent. Therefore, "bare" nanoparticles and coated nanoparticles will absorb at different wavelengths. This allows delivery of optical energy selectively to one type of particles and not the other. Applications include (i) elimination of "bare" nanoparticles from the mixture with coated nanoparticles, (ii) targeting with laser energy only nanoparticles attached to the cell surface or surrounded by proteins or lipids and not particles in the blood stream.

We conclude from this Example that a preferred nanoparticle that possesses a strong narrow band absorption in the near-infrared spectral range is an elongated non-spherically symmetric nanoparticle, such as nano-rod, nano-ellipsoid, nano-paralellepiped or nano-polyhedra. Variation of a nanoparticle aspect ratio permits tuning optical absorption band to a desirable wavelength of electromagnetic radiation.

The particles listed above also can be made as hollow or filled shells. Metal shells with dielectric core have been described (Halas-2002, U.S. Pat. No. 6,344,272). With this example we attract attention to dielectric shells with metal core. Variation of dielectric nanoshell thickness permits finetuning of the optical absorption maximum in the near-infrared spectral range. Thus, both shell thickness and the aspect ratio can be employed for optimizing the design of nanoparticles for the optoacoustic contrast agent.

Figure 6:
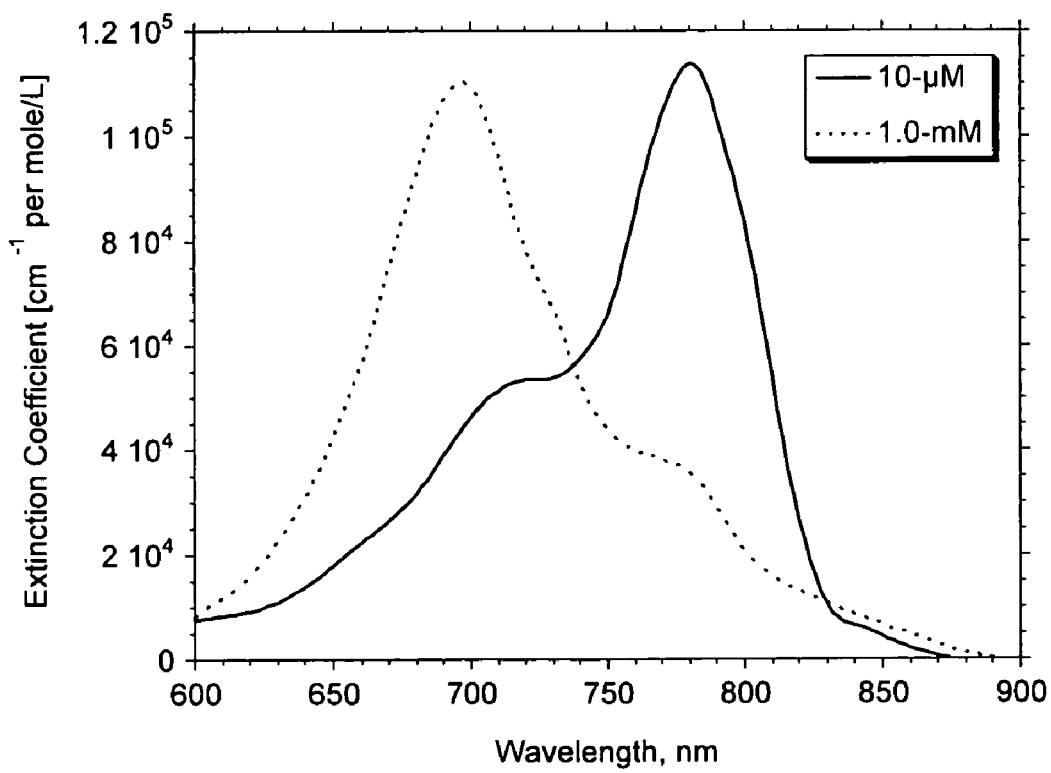
FIG. 6. Optical absorption spectrum of indocyanine-green dye. Maximum extinction coefficient of a 1-molar solution of ICG is about 110,000 $cm^{-1}$.

We have discovered that gold nanoparticles and preferably prolate nanoparticles such as nanorods or ellipsoids and preferably prolate dielectric shells with gold core possess exceptionally strong optical absorption in the near infrared spectral range. This absorption is so high, that no organic molecules or even nanoparticles made of organic substances such as dyes possess optical absorption in the near-infrared range that close to that of gold nanorods (or ellipsoids of revolution) or any other two- or three-dimensional structures based on prolated nanoparticles. As an example, let us compare optical extinction coefficient of the indocyanine-green (ICG) dye, an organic molecule that is known to have very high near-infrared absorbance (see spectrum presented in FIG. 6). ICG maximum molar absorbance is about $1.1 \cdot 10^5$ cm$^{-1}$. To compare, maximum molar absorbance of gold nanoellipsoids of revolution (as depicted in FIG. 2) equals $5.8 \cdot 10^{11}$ cm$^{-1}$. This value can be calculated as a product of maximum absorption cross-section for gold nanoellipsoids ($9.7 \cdot 10^{-10}$ cm$^2$) multiplied by the number of nanoellipsoids in 1-cm$^3$ volume ($6 \cdot 10^{20}$) having concentration of 1 mole per litre. Thus, the absorbance of 1 M nanoellipsoids is about 50 million times stronger than that of 1 M of ICG. Even when the difference in volume of ICG molecules ($V_{ICG} \approx 3$ nm$^3$) relative to the volume of nanoparticles ($V_{NP} \approx 30500$ nm$^3$) is taken into account, the difference in absorption coefficient is still over 5,000 times. Since delivery of any contrast agent (whether molecules or particles) to a desirable type of tissue is always limited, it would be beneficial for an imaging technology to employ contrast agents with greater contrast (i.e. absorption) per particle.

EXAMPLE II

Enhancement of Optoacoustic Signal at 532 nm with Contrast Agents Made of Metallic Nanoparticles.

If the optical fluence exceeds the threshold of phase transition for a substance covering the nanoparticles (let us for the purpose of this example assume that the substance surrounding nanoparticles is water) the amplitude of the optoacoustic signal can be increased one order of magnitude or more. Let us assume that the temperature of the nanoparticle and surrounding water comes to boiling point at some moment $t_{ev}$ in a course of the laser pulse. A thin vapor layer may be generated around the particle heated above 100° C., or water may occur in the superheated steady state. Due to lower heat conductivity of vapor compared to that of water, the temperature of the particle may continue to increase in the course of laser pulse with fluence exceeding the threshold. After the end of the laser pulse the particle temperature relaxes to the initial value due to heat flux from the particle through the vapor layer into the water.

The total mass of vapor is determined by the heat transmitted from the particle to surrounding water and the surface tension of water. In the course of relaxation at some moment of time the temperature of the particle becomes lower then the boiling point and condensation of the vapor starts. Total mass of vapor produced around single particle does not exceed the following value:

$$m_v = \sigma \Phi_0 / \lambda \quad (14)$$

where $\lambda$ is the specific heat of evaporation. We neglect the heat contained in the particle and water surface tension.

The pressure wave, generated by heated elementary volume can be taken in the form:

$$p' = \frac{\rho}{4\pi r} \frac{d^2(\delta V)}{dt^2} \quad (15)$$

where $\delta V$ is the variation of the elementary volume due to thermal expansion and vapor production.

In case of homogeneous bulk absorption of light the expansion of an elementary volume, $\delta V$, can be expressed as:

$$\frac{\delta V_1}{a^3} = \frac{\beta}{\rho c_p} \mu_a \Phi_0 \quad (16)$$

where $\beta$ is the volume expansion coefficient. Thermal expansion coefficient depends on the temperature and for water this dependence is quite strong as known to those skilled in this area of art. Therefore, before the temperature of the particle can reach the boiling point, the efficiency of the optoacoustic generation increases more than 3 times.

The thermal sources, producing the acoustic wave can be described as follows:

$$\beta \delta T = \left(\beta_0 + \frac{d\beta}{dT} \delta T\right) \delta T. \quad (17)$$

Expression (9) shows, that for a small increase of temperature $|\beta_0^{-1} d\beta/dT\ \delta T| \ll 1$ the first term in the brackets dominates the second term, and the distribution of heat sources is proportional to the temperature-rise, $\delta T$. In the opposite case of a substantial temperature-rise $|\beta_0^{-1} d\beta/dT\ \delta T| \gg 1$, and the second term is much greater then the first term, yielding the distribution of heat sources proportional to $\delta T^2$. Thus for short laser pulses the spatial distribution of heat sources will be a sum of two exponents:

$$\beta \delta T = \frac{\mu_a \Phi_0}{\rho c_p} \beta_0 e^{-\mu_a z} + \left(\frac{\mu_a \Phi_0}{\rho c_p}\right)^2 \frac{d\beta}{dT} e^{-2\mu_a z}. \quad (18)$$

For a small temperature-rise (low laser fluence) the leading edge of the optoacoustic signal (that resembles the spatial distribution of heat sources) will have exponential shape with the $\exp[\mu_a c_0 t]$. At higher fluences the exponential slope will become two times sharper: $2\mu_a c_0 t$. In the case of heterogeneous medium with absorbing centers, the variation of the elementary volume due to vapor production can be estimated as (we consider that the pressure is relaxed by that moment):

$$\frac{\delta V_2}{a^3} = \frac{\mu_a \Phi_0}{\rho_v \lambda} \qquad (19)$$

where $\rho_v$, is the vapor density. Heating of the vapor will give further rise to the elementary volume:

$$\frac{\delta V_3}{a^3} = \frac{\mu_a \Phi_0}{p_0} \frac{\gamma - 1}{\gamma} \qquad (20)$$

where $\gamma$ is the adiabatic exponent, $p_0$ is the ambient pressure.

The theoretical model presented above permits estimation of the optoacoustic efficiency for various mechanisms of the thermomechanical phenomena. Volume deformation per unit of specific heat released in various mechanisms is presented in the Table below.

| Optoacoustic efficiency | Water thermal expansion | Vapor production via phase transition | Vapor thermal expansion |
|---|---|---|---|
| $\delta V/\mu_a \Phi_0 a^3$, cm³/J | $8.6 * 10^{-5}$ | $3.2 * 10^{-1}$ | 1.7 |

Thus, heating of nanoparticles through optical absorption can enhance the efficiency of optoacoustic generation up to several orders of magnitude, but this process has an energy fluence threshold dependent on laser pulse duration, size of the particle and the optical absorption coefficient of the particles.

In this example, we demonstrate experimentally that the effectiveness of optoacoustic imaging can be further enhanced through highly localized superheating of NPs resulting in evaporation of a nanolayer of surrounding water, which produces acoustic waves up to an order of magnitude stronger than that from a homogeneously absorbing solution with equal average absorption coefficient.

One skilled in the art can conclude that due to the fact that plasmon absorption of gold nanoparticles is much stronger than optical absorption of organic dyes, a very small concentration of NP's accumulated in an object of a body will make this object detectable with LOIS (assuming absence of NP's in other parts of the body). FIG. 7A shows the advantage of gold NP's relative to an organic dye (such as indocyanine green) as an optoacoustic contrast agent. Not only does the organic dye have three orders of magnitude lower absorption in the near-infrared spectral range (ICG is one of the strongest chromophores reported in the literature with absorption coefficient $\mu_a \approx 1.2 \cdot 10^5$ cm$^{-1}$), but also about 8 times lower optoacoustic efficiency (due to the nonlinear optoacoustic effect in superheated nanoparticles).

Figure 7B:
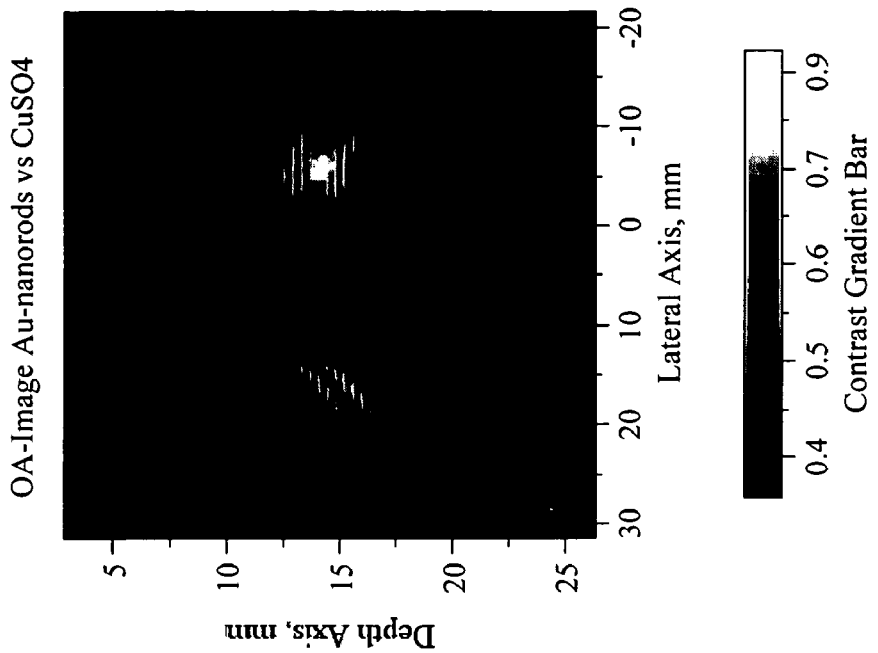
FIG. 7B. Optoacoustic image of gel phantom with embedded gold nanorods with aspect ratio 8 and aqueous CuSO4 solution of similar absorbance at the wavelength of 1064-nm. The image of nanorods is about 2 times brighter.
Figure 7A:
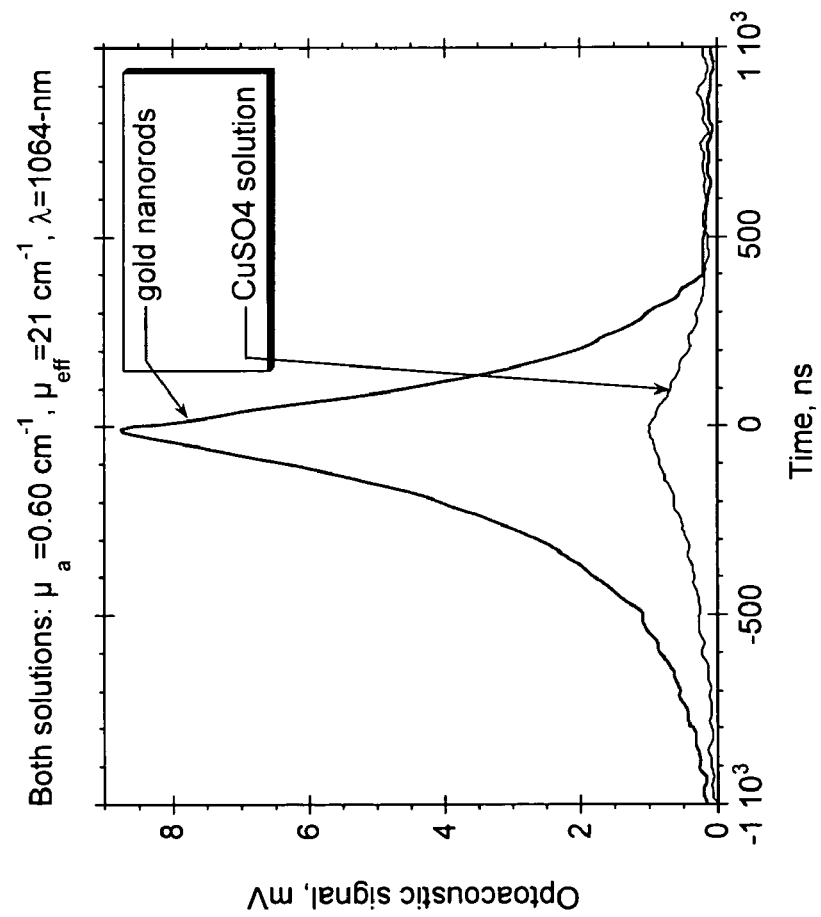
FIG. 7A. Optoacoustic signals detected in dye solution vs. nanosphere suspension of equal absorption. The optoacoustic amplitude in case of nanoparticles exceeds that of dye solution approximately 8 times.

FIG. 7B depicts a two dimensional optoacoustic image with two objects having equal optical absorption of ~1 cm−1 and equal dimensions. One object (on the left) was filled with aqueous solution of CuSO$_4$ and the other object (on the right) was filled with gold nanorods with aspect ratio of 8. The optical fluence from a nanosecond Nd:YAG laser employed for illumination of this phantom was 39 mJ/cm$^2$. One can see a clear difference in the brightness of the two objects. The object filled with gold nanoparticles is much brighter. The difference in the brightness also results in visibly smaller dimensions for the object filled with homogeneously absorbing solution of CuSO$_4$. This is due to poor color resolution (dynamic range) of the image display.

Figure 8A:
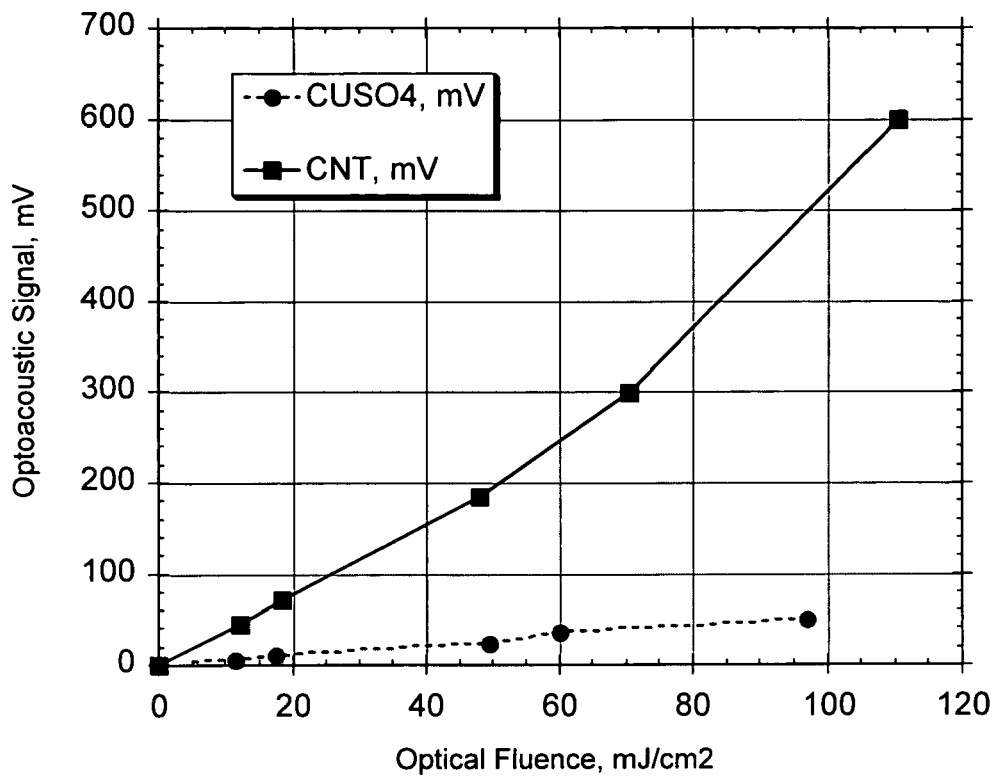
FIG. 8A. Optoacoustic signal amplitude as a function of optical fluence in water suspension of carbon nanotubes (solid line) and in a solution of CuSO4 (dashed line).

Another example of how nanoparticles absorbing near-infrared electromagnetic radiation can enhance brightness of optoacoustic (optoacoustic) images is presented by FIG. 8A. As depicted in FIG. 8A, laser pulse interaction with carbon nanotubes in water suspension results in exceptionally strong optoacoustic signals. While the signal detected in an aqueous solution of CuSO$_4$ follows the theory of linear thermoelastic expansion, the optoacoustic signal amplitude detected in a suspension of single walled carbon nanotubes is much higher than that predicted by the linear theory of thermoelastic expansion. The difference increases with increasing optical fluence. Therefore, in a medical imaging procedure, the optoacoustic amplitude from carbon nanotubes can be much higher than the optoacoustic amplitude from a molecular organic dye with similar absorption.

Figure 8B:
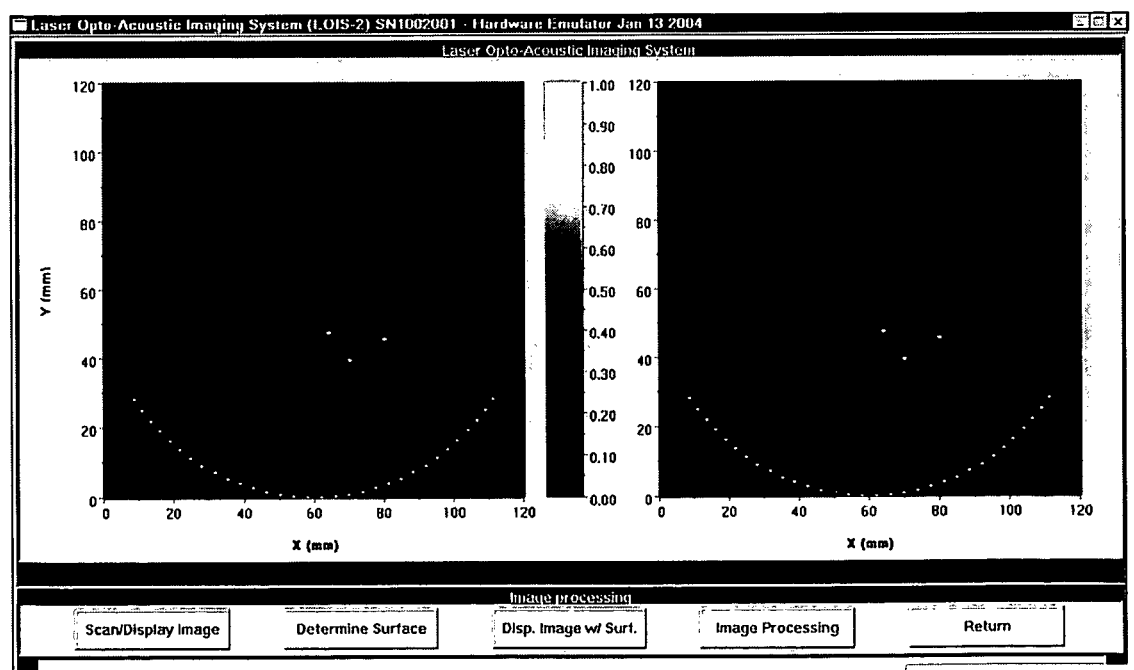
FIG. 8B. Two-dimensional optoacoustic images of three pins made of a polymer filled with single wall carbon nanotubes embedded at a depth of 5 cm inside gel phantom simulating normal tissue. Left panel is raw image and right panel is the same image with background removed.

A similar effect is demonstrated on two-dimensional optoacoustic image, FIG. 8B, where 3 very small objects (diameter of the three objects was less than 1 mm) were visualized at the depth of 5 cm inside a gel phantom simulating biological tissue using the LOIS system with 32 transducers and a very low optical fluence of only 1 mJ/cm$^2$. This result demonstrates the potential of sensitive detection of small objects (inside human or animal body) targeted with nanoparticular contrast agent based carbon nanotubes.

The core substance is also an important parameter for optoacoustic contrast agents. Not only can a core substance influence optical properties of the nanoshells or nanotubes, but also the core substance can play an important role in generation of enhanced laser-induced acoustic signals.

EXAMPLE III

Optoacoustic Biosensor for Detection of Biological Warfare

Optoacoustics technique that employs laser pulses for spectrally selective excitation of multicomponent medium and detection of resulting acoustic waves is well known for its exceptional sensitivity in measuring small concentration of molecules in liquids and gases (Tam, 1986; Zharov and Letokhov, 1984). The method of optoacoustic tomography developed by Oraevsky et al (U.S. Pat. No. 5,840,023) permits sensitive detection, high contrast visualization and diagnostics of early malignant tumors in human organs (Oraevsky 1994, 1996, 2000, 2002). We teach here that resolution and sensitivity of this method can be further enhanced through selective administration of non-spherical gold nanoparticles into the volume of diagnostic interest. Gold nanoparticles help to dramatically enhance the optoacoustic contrast, since they can be designed to strongly absorb laser radiation in the near-infrared spectral range and, being heated by pulses of electromagnetic radiation, effectively generate transient ultrasonic waves in aqueous media. The resulting acoustic (ultrasonic) transients can be detected with specially designed ultrawide-band piezoelectric transducers. Technological advances mentioned above create physical basis for the optoacoustic nanobiosensor that can be utilized in real-time detection of small concentration of strongly infectious and lethal viruses and bacteria, such as smallpox, anthrax and other potential agents of biological warfare.

Figure 9A:
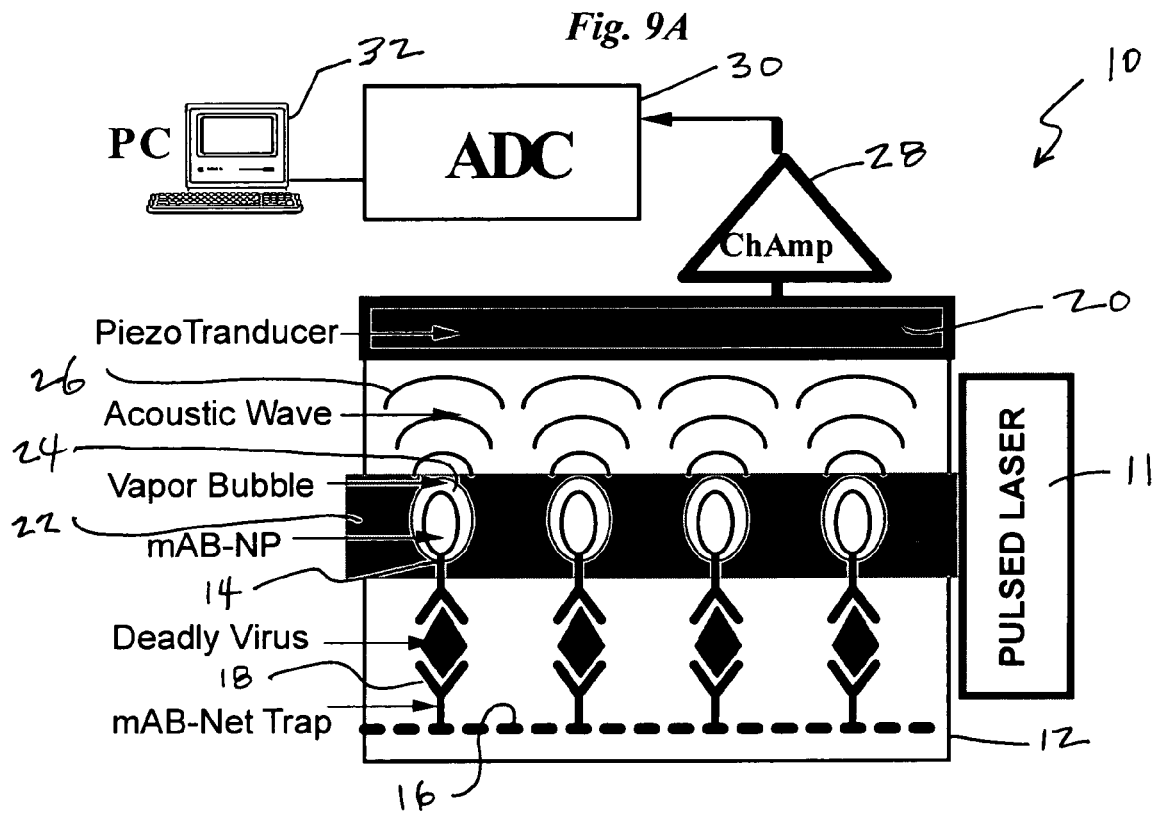
FIG. 9A. Schematic diagram of the optoacoustic nanobiosensor.
Figure 9B:
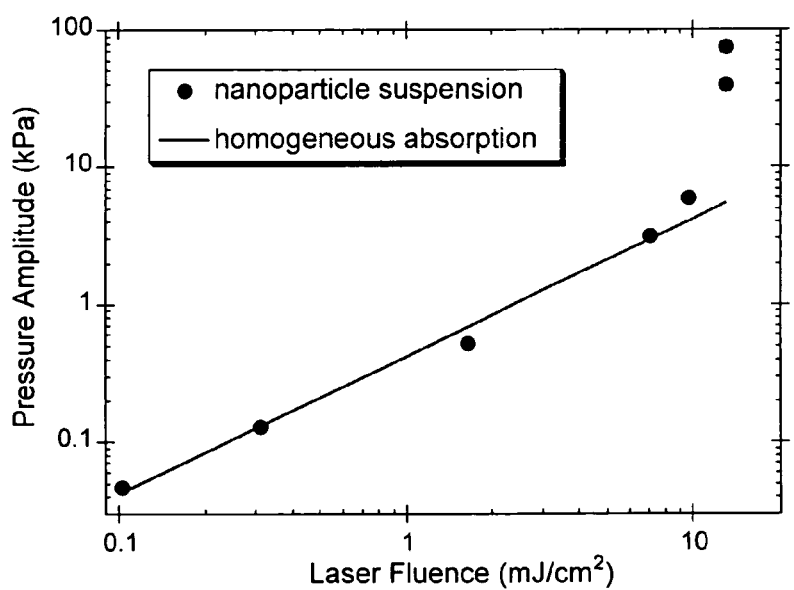
FIG. 9B. Optoacoustic signal from nanoparticles as a function of irradiation fluence.

A schematic diagram of the bio-warfare detection technology is depicted in FIG. 9A. The measurement procedure with the optoacoustic nanobiosensor 10 includes the following steps. A sample of aerosols or water suspected to contain bio-warfare agents, e.g. DMO, is collected and mixed in water with gold nanoparticles (NP) 14 conjugated to a monoclonal antibody (mAB) against specific type of DMO in order to link NP with DMO. Gold nanoparticles as shown in Example I possess a plasmon resonance of optical absorption that can be shifted to any desirable wavelength between green spectral range (convenient for application of pulses of the second harmonic from a Nd:YAG laser), and near-infrared spectral range (convenient for application of a Nd:YAG laser operating at fundamental wavelength). In the event of water contamination, sufficiently excessive concentration of nanoparticles will permit targeting and linkage of all DMO in the probe to NP conjugated with mAB. At the next step, a net-membrane 16 with attached DMO-traps 18 based on the secondary antibody is inserted and moved through the contaminated aqueous suspension. Only DMO complementary to the secondary antibody will be trapped on the net-membrane 16 providing specificity of this method. NP not conjugated with DMO will not be trapped. The net-membrane 16 with trapped DMO linked to NPs is then placed in the detection chamber 12 in acoustic contact with piezoelectric transducer 20. Illumination of the area of DMO-traps with laser pulses 22 from pulsed laser 11 at the wavelength matching resonant absorption of gold nanoparticles generates an expanding vapor bubble 24 produced by thermal energy transfer from superheated nanoparticles to water. Plasmon resonance in gold nanoparticles yields extremely high optical absorption coefficient (>107 cm−1), which permit heating or even superheating of NP with low laser energy. NP superheated with laser pulse can evaporate a surrounding layer of water, which results in generation of transient pressure waves and ultrasonic pulses 26 (so called Giant Optoacoustic Effect) (Diebold, 1990; Oraevsky, 2001). As demonstrated by our experiment depicted in FIG. 9B, the efficiency of ultrasonic generation by expanding vapor upon phase transition (1.7 cm3/J) exceeds that of linearly thermally expanding liquids and solids (<9·10−5 cm3/J) several orders of magnitude. Giant ultrasonic pulses 26 are detected by a wide-band acoustic (piezoelectric) transducer 20, amplified with a charge-amplifier (ChAmp) 28, digitized with analog-to-digital converter (ADC) 30 and processed with a microcomputer 32. Gold nanoparticles heated below melting temperature will not be destroyed by collapse of laser-induced cavitation bubbles. Therefore, the detection process can be repeated in order to increase the signal-to-noise ratio and perform statistical analysis of the optoacoustic signals. Sensitivity of the proposed method significantly exceeds that of the known art and allows detection of a single nanoparticle (single DMO). The concentration of DMO can be determined based on the calibration curve of the optoacoustic signal amplitude as a function of DMO concentration in contaminated samples (Egerev 1992, 2000).

Our computations performed using equations and analytical expressions deducted in Example II showed that laser superheating of gold nanoparticles leads to vaporization of a water nonolayer heated to the temperature of critical point. The resulting pressure is measured in kilobars and depends on nanoparticle radius and the laser pulse duration.

Figure 10A:
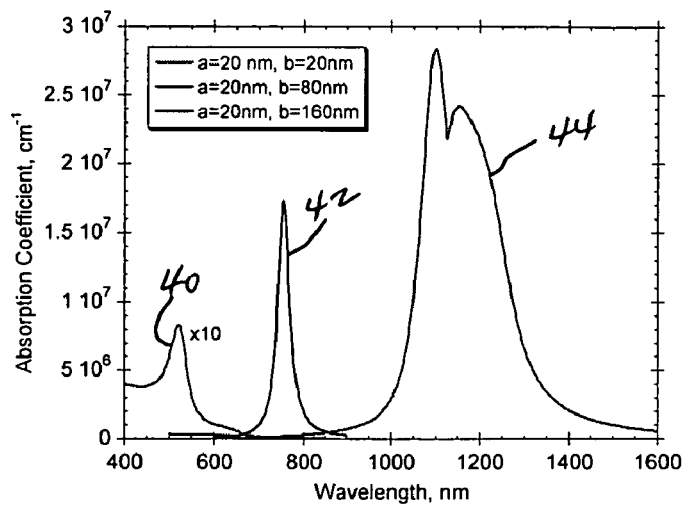
FIG. 10A. Absorption spectra of gold nanoparticles (20-nm radius sphere, ellipsoid of rotation with eccentricity of 4, short wire with aspect ratio of 8).
Figure 10B:
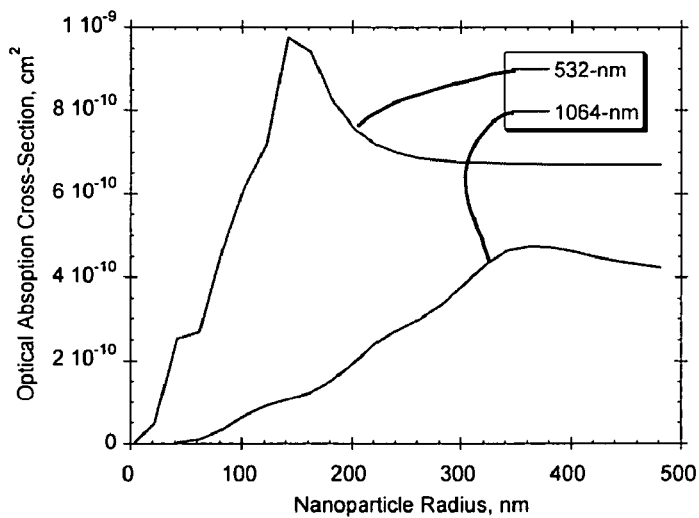
FIG. 10B. Absorption cross-section as a function of sphere radius for 2 wavelengths (532-nm, 1064-nm).
Figure 10C:
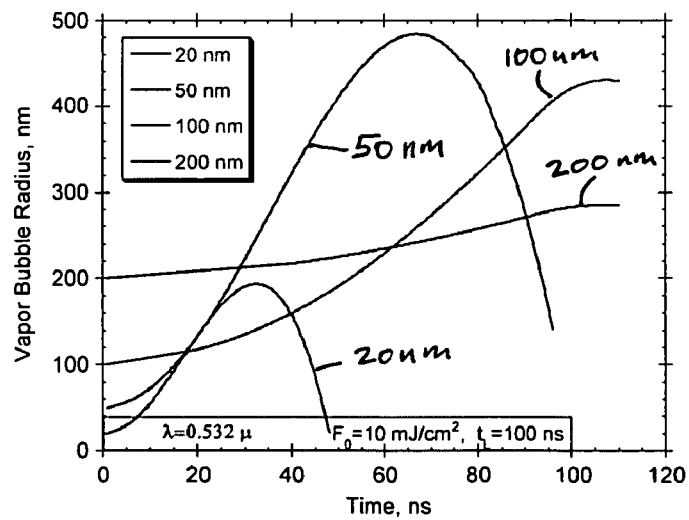
FIG. 10C. Vapor bubble radius as a function of time upon pulsed laser irradiation with the wavelength of 532-nm and fluence of 10 $mJ/cm^2$.

Surprisingly, we discovered that several interesting effects exist in the course of laser energy interaction with gold nanoparticles:

(1) the absorption spectrum of gold nanoparticles is defined by their shape, such as sphere 40, ellipsoid 42 or cylinder 44 (see FIG. 10A), (2) the absorption cross-section at a given wavelength depends on characteristic size of NP (FIG. 10B), and (3) optimal dimensions of nanoparticles exist for each laser irradiation fluence that result in maximum radius of the vapor bubble and in turn, maximum optoacoustic amplitude (FIG. 10C).

The main conclusion of our studies was that the phenomena, which occur in the course of laser pulse interaction with nanoparticles can be employed for optimization of the NP dimensions, shape and structure (see FIG. 10A) and laser irradiation conditions (such as fluence and pulse duration) in order to maximize the resulting ultrasonic signal for detection of NP with ultimate sensitivity. For example, results of our calculations indicated that absorption coefficient of gold NP initially increases with increase of NP radius, then saturates as a consequence of so-called skin effect, i.e. limited effective penetration depth of electromagnetic energy in metals. It is interesting finding that the optimal NP radius in terms of optical absorption coefficient (FIG. 10B) approximately corresponds to an optimal NP radius for generation of maximum size of vapor bubble (FIG. 10C). The laser-induced pressure generated upon giant optoacoustic effect in gold nanoparticles can be very high (up to 10 kbar). However, 1/r-decrease of the optoacoustic amplitude upon spherical ultrasonic wave propagation from a nanoparticle to the transducer may significantly reduce the detected amplitude depending on the distance between the particle and the piezoelectric detector.

EXAMPLE IV

Sensitive Optoacoustic Detection of Gold Nanoparticles in Tissue-Like Gel Phantom A gelatin phantom was prepared with optical properties similar to the properties of biological tissue and six cylindrical objects filled various concentration of spherical gold nanoparticles of 40-nm in diameter have been embedded in the phantom. The NP concentrations were varied in the range from $1.0 \cdot 10^9$ NP/cm$^3$ to $1.3 \cdot 10^{10}$ NP/cm$^3$.

Figure 11A:
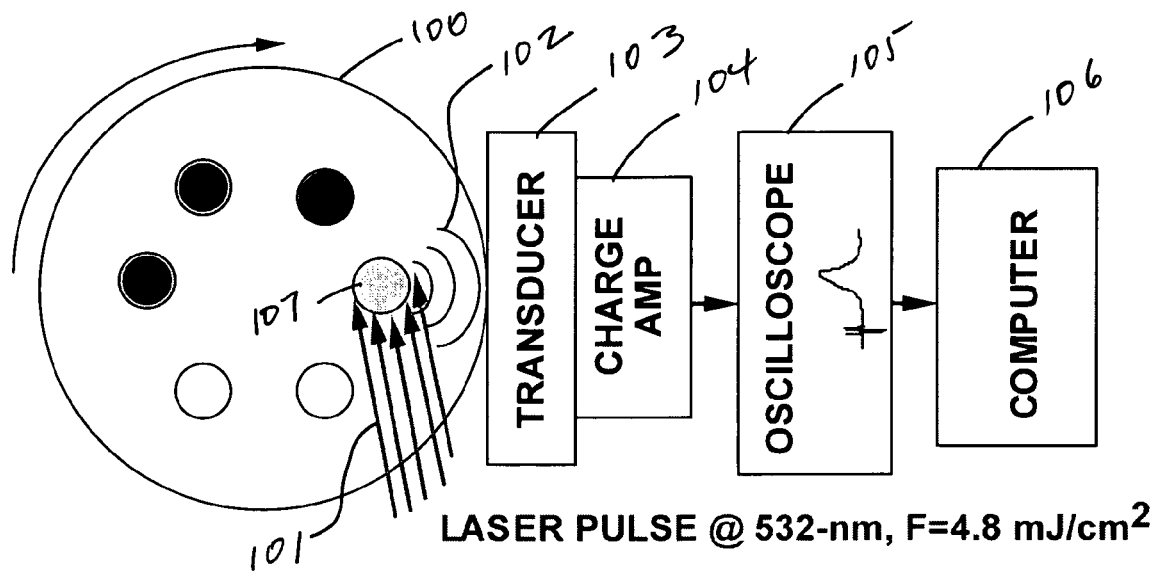
FIG. 11A. Schematic diagram

Referring to FIG. 11A, nanosecond laser pulses at the wavelength of 532-nm were delivered to the phantom surface 100 with energy fluence of 4.8 mJ/cm$^2$, as indicated at 101, so that the entire area of an embedded 5-mm object 107 was illuminated. The resulting pressure (optoacoustic) transient waves 102 propagated to the phantom surface and were detected with an ultrawide-band acoustic transducer 103, amplified by a charge amplifier 104, passed to an oscilloscope 105 and read by a computer 106.

Figure 11B:
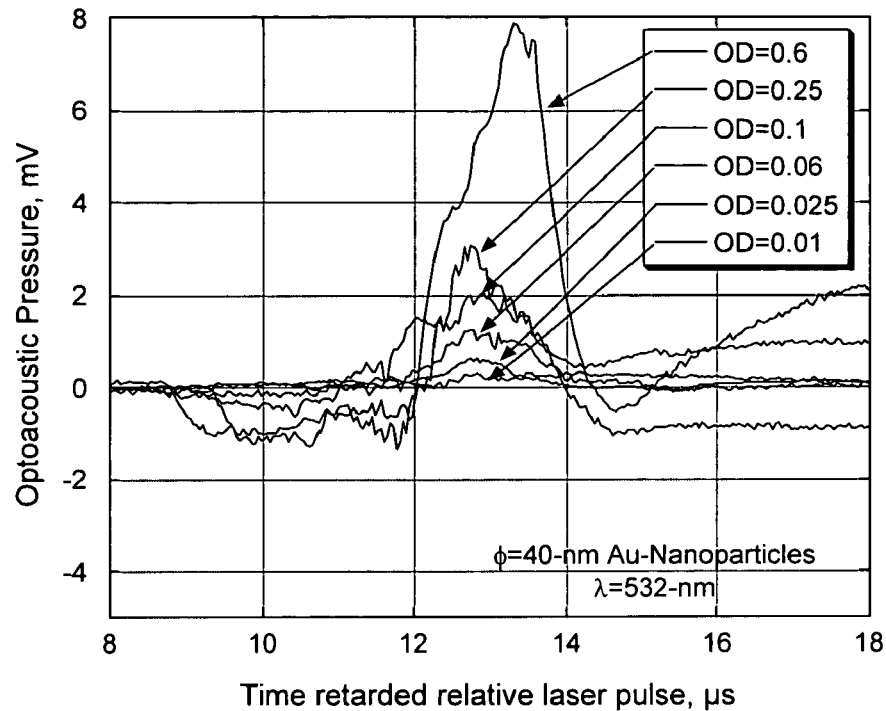
FIG. 11B. Optoacoustic signals detected from a gel phantom with model tumors filled with nanospheres of various concentrations from $10^{10}$ to $10^8$ $NP/cm^3$.
Figure 11C:
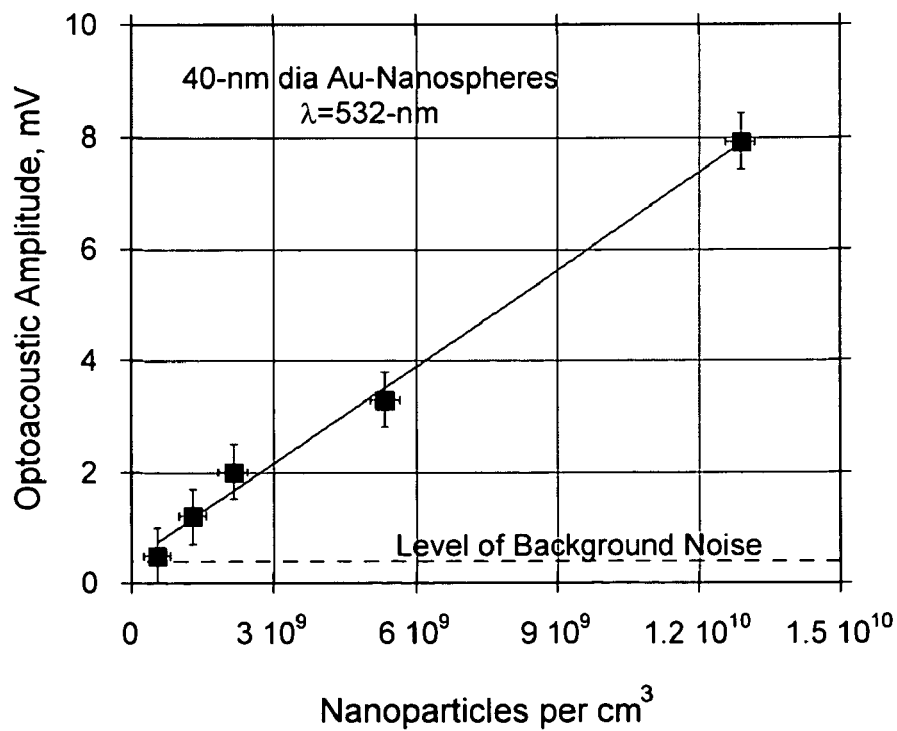
FIG. 11C. Amplitudes of the same signals as in FIG. 11B plotted as a function of nanoparticles concentration.

The measured optoacoustic profiles are presented in FIG. 11B. The optoacoustic amplitude is depicted in FIG. 11C as a function of nanoparticles concentration.

This experiment demonstrated that gold nanoparticles could be reliably imaged in concentrations that are realistic to expect in biological tissues of diagnostic interest upon administration of nanoparticulate contrast agent. As shown at Example I, the signal strength for a gold nanorod is much higher than for a gold sphere. The same technique used in this Example IV will produce a much more sensitive signal with a gold nanorod. Assuming an average cell volume of 1000 μm3, one can calculate that a nanoparticles concentration of 109 per cm$^3$ yields about 1 nanoparticle per cell. This means that optoacoustic imaging using nanoparticulate contrast agent provides close to ultimate sensitivity of detection.

EXAMPLE V

Optoacoustic Imaging of Cancer Cells Selectively Targeted with Gold Nanoparticles One of the important considerations for optoacoustic (optoacoustic) imaging is sensitivity for small object detection in the body. We performed a pilot experiment in vitro that demonstrated the potential of optoacoustic imaging combined with gold nanoparticles as contrast agent in detection of clusters of cancer cells. FIG. 7 depicts an optoacoustic image of the gel phantom with three embedded objects. A slab-shaped gel phantom with diameter of 12-cm, thickness of 9-cm and approximate volume of 1 liter) placed on the arc-shaped optoacoustic transducer array (a) and an optoacoustic image of the same phantom (b). Top 3-cm of the gel phantom was sliced to produce flat surface for the laser illumination. The phantom was illuminated from the top with laser pulses at the wavelength of 532-nm. Laser beam had a Gaussian cross-section with incident energy fluence of 10 mJ/cm$^2$ and diameter of 30-mm (visible as a light smeared line in the upper part of the optoacoustic image). Phantom was made using 90 g of gelatin powder (Sigma, St. Louis, Mo.), 10 mL of the whole milk (Oak Farms, Dallas, Tex.) and water.

Figure 12A:
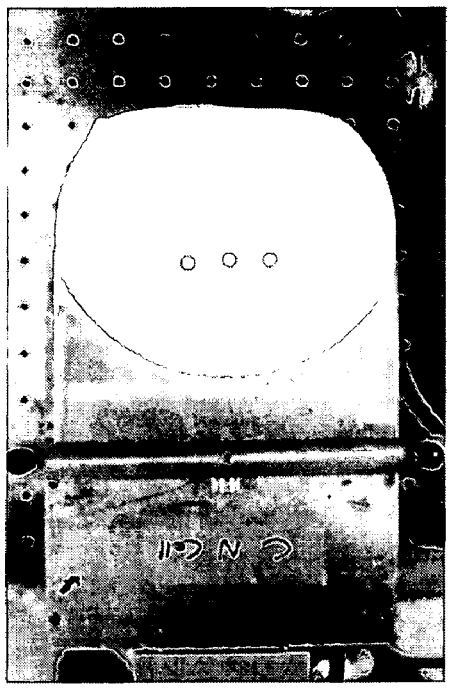
FIGS. 12A and 12B. Photograph of a gel phantom and an optoacoustic image of the same phantom, respectively. Three tubes made of thin transparent plastic were embedded in the gel and visualized by LOIS. These tubes were filled with three media: same gel as used in the phantom (left), gold 40-nm spherical nanoparticles in concentration of $10^9$ $NP/cm^3$ (center) and breast cancer SK-BR3 cells targeted with gold nanoparticles (right).

Referring to FIG. 12A, three tubes with internal diameter of 4-mm and length of 11-mm were embedded in the center of the phantom at the depth of 5-cm from the illuminated surface and 4-cm from the array of transducers. These tubes were filled with three media: same gel as used in the phantom (left), gold 40-nm spherical nanoparticles in concentration of $10^9$ NP/cm$^3$ (center) and breast cancer SK-BR3 cells targeted with gold nanoparticles (right). Two of the three objects can be clearly visualized. The third invisible object served as control of the fact that a thin-wall plastic tube used to contain cancer cells did not have sufficient optoacoustic contrast.

Figure 12B:
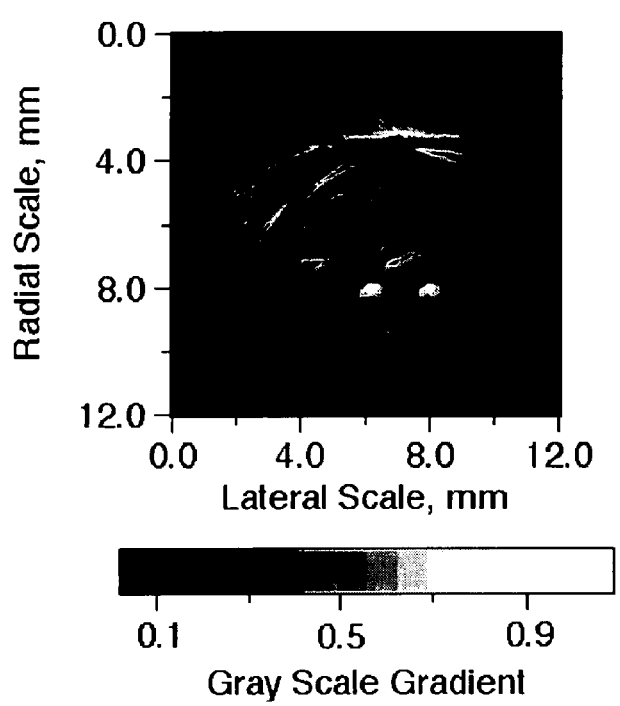

Referring to FIG. 12B, The main result of this experiment is a demonstration that SK-BR3 breast cancer cells can be (1) successfully targeted by biotinylated Herceptin antibody, (2) further targeted with 40-nm gold nanoparticles conjugated with streptavidin, and (3) detected and imaged with laser optoacoustic imaging system (LOIS) in a gel phantom at a depth of at least 5 cm. Optical properties of the phantom at the wavelength of 532-nm resembled optical properties of the breast tissue in the near-infrared spectral range (effective optical attenuation was $\mu_{eff}=1.4$ cm$^{-1}$ dominated by optical scattering). Optical properties of the aqueous suspension of gold nanoparticles were $\mu_a=0.12$ cm$^{-1}$ and $\mu_s^1=0$. Optical properties of the cluster of cells were unknown. However, visually the sample of cells was pink having slightly lighter hue compared with the suspension of gold nanoparticles. Spatial distribution of the pink color through the sample of cells was heterogeneous with about half of cells pink and the other half light cream. Visual description of the cells matched with optoacoustic image being slightly lower brightness and smaller diameter (right) compared with the reference tube containing gold nanoparticles (center). Using non-spherical nanoparticulates of this invention, the signals are greater and the sensitivity of the test is improved.

REFERENCES CITED

M. Aslam "Bioconjugation: protein coupling techniques for the biomedical sciences," Macmillan Reference, New York, 1998.

S. B. Abrams Laser-based breast imager competes with X-rays, Biophotonics International, 1997, 4(1): 21-22.

J. E. Beesley Colloidal Gold: A New Perspective for Cytochemical Marking," Oxford, New York, 1989.

G. Blume, G. Ceve Biochim. Biophys. Acta 1990, 1029, 91-97.

S.-S. Chang, C.-W. Shih, W.-C. Lai, C. R. C. Wang *"The Shape Transition of Gold Nanorods", Langmuir,* 1999, 15, 701-709.

S.-S. Chang et. al., Langmuir 1, 1999, 15, 701.

E. Dujardin, L.-B. Hsin, C. R. Chris Wang, S. Mann "DNA-driven self-assembly of gold nanorods", Chem. Commun., 2001, 1264-1265.

G. J. Diebold, T. Sun "Properties of optoacoustic waves in one, two, and three dimensions," Acustica, 1994; 80, 339-351.

G. J. Diebold, M. I. Khan, S. M. Park: "Photoacoustic signatures of particulate matter: optical production of acoustic monopole radiation", Science 1990; 250: 101-104.

F. A. Duck, Physical properties of tissue: A comprehensive reference book, Academic Press, San Diego, 1990.

S. V. Egerev, and A. V. Fokin in *Biomedical Optoacoustics*, ed. by A. A. Oraevsky, *Proc. SPIE,* 2000, v. 3916, pp. 210-217.

S. V. Egerev, O. M. Zozulya, and O. V. Puchenkov: Sensitive wide-band ultrasonic detection of particles in liquids, In Photoacousic and Photothermal Phenomena III, Springer, New-York-Heidelberg, 1992, pp. 50-52.

Eur. Pat. EP0601618

Eur. Pat. EP0602700

Eur. Pat. EP0808175

M. A. Eghtedari, J. A. Copeland, V. L. Popov, M. Motamedi, N. Kotov, A. A. Oraevsky: Bioconjugated gold nanoparticles as a contrast agent for optoacoustic detection of small tumors, Proc. SPIE 2003, 4960: 76-85.

R. Gans: Ann. Phys. 1915, 47, 270

R. T. Greenlee, M. B. Hill-Harmon, T. Murray, M. Thun "Cancer statistics 2001," *CA Cancer J. Clin.,* 2001; 51, 15-36.

G. Gregoriadis, B. McCormack, Targeting of Drugs 6: Strategies for Stealth Therapeutic Systems, Plenum, 1998, pp. 264-267.

J. F. Hainfeld, Scanning Microsc., 1995, 239, 254.

M. Harris, J. (ed) "Poly(ethylene glycol) chemistry, biotechnical and biomedical applications" Plenum Press, New York, 1992.

M. A. Hayat Colloidal Gold: Principles, Methods, and Applications Vol. 3, Academic Press, New York, 1985.

M. Harris, J. (ed) "Poly(ethylene glycol) chemistry, biotechnical and biomedical applications" Plenum Press, New York, 1992.

S. Hsieh, S. Meltzer, C. R. C. Wang, A. A. G. Requicha, M. E. Thompson, B. E. Koel *J. Phys. Chem.,* 2002, 106, 231.

R. Jin, Y. Cao, C. A. Mirkin, K. L. Kelly, G. C. Schatz, J. Zheng *Science,* 2001, 294, 1901.

A. Kameo, A. Suzuki, K. Torigoe, K. Esumi *J. Coll. Interface Sci.,* 2001, 241, 289.

A. A. Karabutov, E. V. Savateeva, V. G. Andreev, S. V. Solomatin, R. D. Y. Fleming, Z. Gatalica, H. Singh, M. P. Henrichs, and A. A. Oraevsky: "Optoacoustic images of early cancer in forward and backward modes", European Conference on Biomedical Optics, Proc. SPIE 2001; 4434: 13-27.

A. A. Karabutov, E. V. Savateeva, A. A. Oraevsky: Optoacoustic supercontrast for early cancer detection, Proc. SPIE 2001; 4256: 179-187.

A. A. Karabutov, A. A. Oraevsky: Ultimate sensitivity of wide-band detection for laser-induced ultrasonic transients, Proc. SPIE 2000; 3916: 228-239.

F. Kim, J. H. Song, P. Yang "Photochemical Synthesis of Gold Nanorods," J. Am. Chem. Soc. 2002, 124, 14316-14317.

A. L. Klibanov, et al. FEBS Letters 1990, 268, 235.

G. Kong, R. D. Braun, M. W. Dewhirst, *Cancer Res.,* 2001, 61, 3027.

G. Kong, R. D. Braun, M. W. Dewhirst, *Cancer Res.,* 2000, 60, 4440.

M. N. V. R. Kumar, *J. Pharm. Pharmaceut. Sci.,* 2000, 3, 234.

Leggett "Optical mammography offers promise as alternative to X-ray detection," *Biophotonics International.,* 1996; 3(1): 56-57.

M. Link, M. W. El-Sayed: Spectral properties and relaxation dynamics of surface plasmon electronic oscillations in gold and silver nanodots and nanorods, J. Phys. Chem. B, 1999, 103, 8410.

S. Link, M. B. M. A. El-Sayed: *J. Phys. Chem. B* 1999, 103: 3073-3077.

M. B. Mohammed, K. Z. Ishmail, S. Link, M. A. El-Sayed, *J. Phys. Chem.*, 1998, 102, 9370.

A. A. Oraevsky, S. L. Jacques, R. O. Esenaliev, F. K. Tittel: Laser based optoacoustic imaging in biological tissues, *Proc. SPIE* 1994; 2134A: 122-128

A. A. Oraevsky, R. O. Esenaliev, S. L. Jacques, F. K. Tittel, and D. Medina. "Breast Cancer Diagnostics by Laser Opto-Acoustic Tomography", OSA Trends in Optics and Photonics on Advances in Optical Imaging and Photon Migration", R. R. Alfano and J. G. Fujimoto, eds. (OSA, Washington, D.C.), 1996, v. 2, pp. 316-321.

A. A. Oraevsky, A. A. Karabutov, V. A. Andreev, R. O. Esenaliev: Laser opto-acoustic imaging of the breast: Detection of cancer angiogenesis, *Proc. SPIE* 1999; 3597: 352-363.

A. A. Oraevsky, S. L. Jacques, F. K. Tittel "Determination of tissue optical properties by time-resolved detection of laser-induced stress waves, *Proc. SPIE* 1993; 1882: 86-101.

A. A. Oraevsky, R. O. Esenaliev, S. L. Jacques, F. K. Tittel "Lateral and z-axial resolution in laser optoacoustic imaging with ultrasonic transducers," *Proc. SPIE*, 1995, 2389, 198-208, (Appendix).

A. A. Oraevsky, S. L. Jacques, F. K. Tittel, "Measurement of tissue optical properties by time-resolved detection of laser-induced transient stress," *Applied Optics*, 1997, 36(1): 402-415.

A. A. Oraevsky, A. A. Karabutov, E. V. Savateeva Optoacoustic supercontrast for early cancer detection," *Proc. SPIE* 2001; 4256, 179-187.

A. A. Oraevsky, A. A. Karabutov, E. V. Savateeva "Enhancement of optoacoustic tissue contrast with absorbing nanoparticles," European Conference on Biomedical Optics, *Proc. SPIE* 2001, 4434, 60-69.

A. A. Oraevsky, A. A. Karabutov, E. V. Savateeva: "Enhancement of optoacoustic tissue contrast with absorbing nanoparticles", European Conference on Biomedical Optics, *Proc. SPIE* 2001; 4434: 60-69.

G. C. Papavassiliou: Optical Properties of small inorganic and organic metal particles, *Prog. Solid State Chem*, 1980, 12,185-286

PCT WO0106257

PCT WO9857667

PCT WO02059226

M. L. Sandrock, C. D. Pibel, F. M. Geiger, C. A. Foss J. Phys. Chem., 1999, 103, 2668.

C.-W. Shih, W.-C. Lai, C.-C. Hwang, S.-S. Chang, C. R. Chris Wang "*Electrochemcial Synthesis and Optical Properties of Au Nanorods*," in *The Handbook of Metal Nanoparticles: Metal Nanoparticles: Synthesis, Characterization, and Applications*" Marcel Dekker, 2001, Chapter 7, pp. 163-182.

J. J. Storhoff, A. A. Lazaorides, R. C. Mucic, C. A. Mirkin, R. L. Letsinger, G. C. Schatz, "What controls the optical properties of DNA-linked fold nanoparticle assemblies?" *J. Am. Chem. Soc.*, 2000, 122, 4640.

J. A. Stratton: "Electromagnetic Theory, McGraw-Hill, New York, 1941.

Y. Sun, Y. Xia "Shape-controlled synthesis of gold and silver nanoparticles," *Science*, 2002, 298, 2176-9.

F. Kim, J. H. Song, P. Yang "Photochemical synthesis of gold nanorods," *J. Am. Chem. Soc.*, 2002, 124(48): 14316-7.

A. C. Tam, "Applications of photoacoustic sensing techniques", Rev. Modern Phys. 58(2), 381-431, (1986).

Thorpe et al. "Breast Cancer Research and Treatment," 1995, 36: 237-51.

B. J. Tromberg, N. Shah, Ryan Lanning, A. Cerussi, J. Espinoza, T. Pham, L. Svaasand, J. Butler "Noninvasive in vivo characterization of breast tumors using photon migration spectroscopy," *Neoplasia*, 2000, 2(1), 26-40.

US Pat. App. 20010002275
US Pat. App. 20020044909.
US Pat. App. 2002022004
US Pat. App. 2002132045
US Pat. App. 20020103517
US Pat. App. 20020160195
US Pat. App. 20020034537
U.S. Pat. No. 5,472,683
U.S. Pat. No. 5,500,204
U.S. Pat. No. 5,521,218
U.S. Pat. No. 5,525,328
U.S. Pat. No. 5,543,133
U.S. Pat. No. 5,447,710
U.S. Pat. No. 5,560,932
U.S. Pat. No. 5,573,783
U.S. Pat. No. 5,580,579
U.S. Pat. No. 5,840,023
U.S. Pat. No. 6,090,858
U.S. Pat. No. 6,123,923
U.S. Pat. No. 6,139,819
U.S. Pat. No. 6,180,085
U.S. Pat. No. 6,180,087
U.S. Pat. No. 6,183,726
U.S. Pat. No. 6,190,641
U.S. Pat. No. 6,264,920
U.S. Pat. No. 6,264,914
U.S. Pat. No. 6,264,917
U.S. Pat. No. 6,264,919
U.S. Pat. No. 6,270,806
U.S. Pat. No. 6,331,289
U.S. Pat. No. 6,344,272
U.S. Pat. No. 6,395,257
U.S. Pat. No. 6,403,056
U.S. Pat. No. 6,428,811

N. Weidner, J. P. Semple, W. R. Welch, J. Folkman "Tumor angiogenesis and metastasis—correlation in invasive breast carcinoma," *New England J. of Med.*, 1991, 324, 1-7.

G.-T. Wei, F.-K. Liu, S.-S. Chang, C. R. C. Wang "*Shape Separation of Nanometer Gold Particles by Size Exclusion Chromatography*" Anal. Chem., 1999, 71, 1085-2091

Y. Y. Yu, S.-S. Chang, C. L. Lee, C. R. C. Wang, *J. Phys. Chem. B*, 1997, 101, 6661.

M. Yamada, A. Kuzume, M. Kurihara, K. Kubo, H. Nishihara "Formation of a novel porphyrin-gold nanoparticle network film induced by IR light irradiation," *Chem. Commun.* 2001, 23, 2476-2477.

B. M. I. van der Zande, M. R. Böhmer, L. G. J. Fokkink, C. Schönenberger, *J. Chem. Phys.*, 1997, 101, 852.

Q. Zhu, E. Conant, B. Chance, "Optical imaging as an adjuvant to sonography in differentiating benign from malignant breast lesions," *J. Biomed. Optics*, 2000, 5, 12-17.

V. P. Zarov, V. S. Letokhov, *Laser opto-acoustic spectroscopy*, (Springer Verlag, Berlin-Heidelberg-New York, 1984), 320p.

The invention claimed is:

1. A method of enhancing detection for a specific object or distribution thereof in a body, comprising the steps of:
   (a) administering to said for detection of the object, if present, a nanoparticulate, the nanoparticulate having the following properties;
      i. it is a collection of at least partially metallic nanoparticles, having a most probable size and most probable absorption maximum at a selected wavelength or range of wavelengths, comprising shells with a negative value of the real part of the complex dielectric permeability wherein said shells are filled with a substance having a coefficient of thermal expansion in the range of 9.times.10.sup-2 mm.sup.3joule to 2.times.10.sup.3 nm .sup.3/joule,
      ii. it has a minimal characteristic dimension in the range from about 1 to about 3000 nanometers, and
      iii. it has a formed composition capable of producing thermal pressure either in said nanoparticulate or in said object greater than said object could produce as a result of step (b) in the absence of said nanoparticulate;
   (b) directing onto said body specific electromagnetic radiation having a wavelength or spectrum of wavelengths in the range from 3 nm to 300 mm selected so that the wavelength or wavelength spectrum is longer by a factor of at least 3 than the minimum characteristic dimension of said nanoparticulate, said nanoparticulate absorbing said electromagnetic radiation more than would one or more non-aggregated spherically shaped particles of the same total volume with a composition identical to said nanoparticulate, said nanoparticulate by such absorption producing an enhanced optoacoustic signal resulting from said absorption;
   (c) receiving said optoacoustic signal;
   (d) converting said received optoacoustic signal into an electronic signal characterized by at least one parameter selected from amplitude, frequency, phase, temporal profile, time of arrival, frequency spectrum, or a combination of any one or more of such parameters; and
   (e) presenting said signal for assessment of said at least one parameter by a human or a machine.

2. The method of claim 1 in which said substance is selected from the group comprising water, aqueous gels, hydrogels, gases, lipids and other organic substances.

3. A method of enhancing detection for a specific object or distribution thereof in a body, comprising the steps of;
   (a) administering to said body for detection of the object, if present, a nanoparticulate, the nanoparticulate having the following properties;
      i. it is a collection of at least partially metallic nanoparticles, having a most probable size and a most probable absorption maximum at a selected wavelength or range of wavelengths, wherein said collection is selected from gold, silver, platinum, a mixture of at least two of said metals, or an alloy of at least two of said metals, or a carbon nanotube with metallic properties
      ii. it has a minimal characteristic dimension in the range from about 1 to about 3000 nanometers, and
      iii. it has a formed composition capable of producing thermal pressure either in said nanoparticulate or in said object greater than said object could produce as a result of step (b) in the absence of said nanoparticulate;
   (b) directing onto said body specific electromagnetic radiation having a wavelength or spectrum of wavelengths in the range from 3 nm to 300 mm selected than the minimum characteristic dimension of said nanoparticulate, said nanoparticulate absorbing said electromagnetic radiation more than would one or more non-aggregated spherically shaped particles of the same total volume with a composition identical to said nanoparticulate, said nanoparticulate by such absorption producing an enhanced optoacoustic signal resulting from said absorption;
   (c) receiving said optoacoustic signal;
   (d) converting said received optoacoustic signal into an electronic signal characterized by at least one parameter selected from amplitude, frequency, phase, temporal profile, time arrival, frequency spectrum, or a combination of any one or more of such parameters; and
   (e) presenting said signal for assessment of said at least one parameter by a human or a machine.

4. A method of enhancing detection for a specific object which may be a tissue, cell, microorganism, or molecule, or bio-warfare agent or distribution thereof in a body, comprising the steps of:
   (a) administering to said body for detection of the object, if present, a nanonarticulate, the nanoparticulate having the following properties:
      i. it is at least partially metallic,
      ii. it has a minimal characteristic dimension in the range from about 1 to about 3000 nanometers, and
      iii. it has a formed composition capable of producing thermal pressure either in a said nanoparticulate or in said object greater than said object could produce as a result of step (b) in the absence of said nanoparticulate;
   (b) directing onto said body specific electromagnetic radiation having a wavelength or spectrum of wavelengths in the range from 3 nm to 300 mm selected than the minimum characteristic dimension of said nanoparticulate, said nanoparticulate absorbing said electromagnetic radiation more than would one or more non-aggregated spherically shaped particles of the same total volume with a composition identical to said nanoparticulate, said nanoparticulate by such absorption producing an enhanced optoacoustic signal resulting from said absorption;
   (c) receiving said optoacoustic signal;
   (d) converting said received optoacoustic signal into an electronic signal characterized by at least one parameter selected from amplitude, frequency, phase, temporal profile, time of arrival, frequency spectrum, or a combination of any one or more of such parameters; and
   (e) presenting said signal for assessment of said at least one parameter by a human or a machine.

* * * * *